United States Patent
Fukuda

(10) Patent No.: US 10,219,758 B2
(45) Date of Patent: Mar. 5, 2019

(54) IMAGE PROCESSING APPARATUS, METHOD, AND PROGRAM

(71) Applicant: FUJIFILM Corporation, Tokyo (JP)

(72) Inventor: Wataru Fukuda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 64 days.

(21) Appl. No.: 15/628,602

(22) Filed: Jun. 20, 2017

(65) Prior Publication Data
US 2018/0055459 A1 Mar. 1, 2018

(30) Foreign Application Priority Data

Aug. 24, 2016 (JP) .................................. 2016-163323

(51) Int. Cl.
*A61B 6/02* (2006.01)
*A61B 6/03* (2006.01)
*G06T 11/00* (2006.01)

(52) U.S. Cl.
CPC ................ *A61B 6/025* (2013.01); *A61B 6/03* (2013.01); *G06T 11/005* (2013.01); *G06T 11/006* (2013.01)

(58) Field of Classification Search
CPC .... G06T 11/003; G06T 11/005; G06T 11/006; G06T 2207/20016; A61B 6/025; A61B 6/03; A61B 6/032; A61B 6/5205
See application file for complete search history.

(56) References Cited

U.S. PATENT DOCUMENTS

| | | | |
|---|---|---|---|
| 2010/0135558 A1 | 6/2010 | Ruth et al. | 382/131 |
| 2010/0220912 A1* | 9/2010 | Bruder et al. | G06T 5/002 382/131 |
| 2012/0321163 A1* | 12/2012 | Akahori | G06T 11/006 382/131 |
| 2015/0302615 A1 | 10/2015 | Fukuda | G06T 11/006 |
| 2016/0206268 A1 | 7/2016 | Fukuda | A61B 6/5235 |
| 2017/0071554 A1* | 3/2017 | Fukuda | A61B 6/02 |

FOREIGN PATENT DOCUMENTS

| | | |
|---|---|---|
| JP | 2014-133095 A | 7/2014 |
| JP | 2015-066344 A | 4/2015 |

* cited by examiner

*Primary Examiner* — Andrew W Johns
(74) *Attorney, Agent, or Firm* — JCIPRNET

(57) ABSTRACT

An image acquisition unit acquires a plurality of projection images by imaging a subject at each of a plurality of radiation source positions. A reconstruction unit reconstructs the plurality of projection images to generate a plurality of tomographic images. A frequency decomposition unit frequency-decomposes each of the plurality of tomographic images to acquire a plurality of band tomographic images, which show frequency components of each of the plurality of frequency bands, for each of the plurality of tomographic images. A two-dimensional image generation unit generates a band synthesized two-dimensional image by projecting the plurality of band tomographic images for each frequency band. A frequency synthesizing unit performs frequency synthesis by weighting the band synthesized two-dimensional image for each frequency band, thereby generating a composite two-dimensional image.

21 Claims, 17 Drawing Sheets

IMAGE PROCESSING APPARATUS, METHOD, AND PROGRAM

CROSS REFERENCE TO RELATED APPLICATIONS

The present application claims priority under 35 U.S.C. § 119 to Japanese Patent Application No. 2016-163323 filed on Aug. 24, 2016. The above application is hereby expressly incorporated by reference, in its entirety, into the present application.

BACKGROUND OF THE INVENTION

Field of the Invention

The present invention relates to an image processing apparatus, method, and program for generating a two-dimensional image, which corresponds to an image acquired by simple imaging, from a tomographic image acquired by tomosynthesis imaging.

Related Art

In recent years, in radiation image capturing apparatuses using radiation such as X-rays, gamma rays, in order to observe an affected part in more detail, tomosynthesis imaging has been proposed in which a radiation source is moved to irradiate a subject from a plurality of radiation source positions to perform imaging and a tomographic image is generated by emphasizing a desired tomographic plane from a plurality of projection images acquired by the imaging. In the tomosynthesis imaging, a plurality of projection images are acquired by imaging a subject at a plurality of radiation source positions while moving a radiation source in parallel with a radiation detector or moving the radiation source so as to draw an arc of a circle or an ellipse according to the characteristics of an imaging apparatus and a required tomographic image, and these projection images are reconstructed using a back projection method, such as a simple back projection method or a filtered back projection method, to generate a tomographic image. By generating such a tomographic image on a plurality of tomographic planes of the subject, it is possible to separate structures overlapping each other in a depth direction in which the tomographic planes of the subject are aligned. Therefore, it is possible to find a lesion that has been difficult to detect in a two-dimensional image acquired by simple imaging in the related art. The term "simple imaging" refers to an imaging method for acquiring one two-dimensional image, which is a transmission image of a subject, by irradiating the subject once.

On the other hand, the tomosynthesis imaging has a problem that a reconstructed tomographic image is blurred due to the mechanical error of the imaging apparatus and the influence of body motion of the subject due to the time difference of imaging at each of a plurality of radiation source positions. When the tomographic image is blurred as described above, it is difficult to find a lesion such as minute calcification, which is useful for early detection of breast cancer, particularly in a case where the breast is a subject. For this reason, in the case of performing tomosynthesis imaging, it is common to perform simple imaging as well to acquire both a tomographic image and a two-dimensional image.

However, when both tomosynthesis imaging and simple imaging are performed, the exposure dose to the subject increases. For this reason, a method has been proposed in which a tomographic image acquired by tomosynthesis imaging is projected in a depth direction in which the tomographic planes of the subject are aligned, thereby generating a two-dimensional image corresponding to a radiation image acquired by simple imaging (refer to US2010/0135558A). Hereinafter, the two-dimensional image generated in this manner is referred to as a composite two-dimensional image.

In addition, a method has been proposed in which a projection image is acquired, frequency processing for attenuating low frequency components of a projection image, of which an angle (hereinafter, refereed to as an incidence angle) of radiation incident on the detection surface of a radiation detector with respect to an axis perpendicular to the detection surface of the radiation detector is large, relative to high-frequency components is performed, a tomographic image in which the amount of artifacts has been reduced is reconstructed from a projection image having a small incidence angle and a projection image subjected to frequency processing, and a composite two-dimensional image is generated from such a tomographic image (refer to JP2014-133095A).

In addition, a method has been proposed in which a first tomographic image that is emphasized according to the spatial frequency and that is used for image interpretation is generated based on a projection image, a second tomographic image in which the degree of emphasis is different from that of the first tomographic image and which is emphasized according to the spatial frequency, and a composite two-dimensional image is generated using the second tomographic image (refer to JP2015-66344A).

Incidentally, in the tomosynthesis imaging, the incidence angle when irradiating the subject is limited. Therefore, for example, in a case where a tomographic image is reconstructed by superimposing projection images using a back projection method, artifacts, which are virtual images of the structure, may be reflected in the depth direction in which the tomographic planes are aligned. More specifically, due to back projection, artifacts may be reflected in a region, in which no structure is present originally, of a tomographic image of a tomographic plane different from a tomographic image of a tomographic plane where a structure is present. In particular, as the size of the structure increases, a range in the depth direction in which artifacts are present increases. For this reason, in a case where a large structure and a small structure are present side by side in the depth direction, if a plurality of tomographic images are simply added up to generate a composite two-dimensional image, the small structure disappears due to the influence of artifacts of the large structure. As a result, it is difficult to check a structure required for diagnosis of a lesion or the like. In addition, the composite two-dimensional image becomes an image of an impression of being blurred.

For this reason, in the method disclosed in US2010/0135558A, a minimum value projection method is used when generating a composite two-dimensional image from the tomographic image. Here, calcification in the breast is a minute region with high brightness (that is, low density) in the projection image. Therefore, if a composite two-dimensional image is generated using the minimum value projection method, it is possible to observe a minute high-brightness region, such as calcification, in the composite two-dimensional image.

SUMMARY

However, when a composite two-dimensional image is generated using the minimum value projection method as in the method disclosed in US2010/0135558A, information regarding the thickness of a subject disappears. As a result, the composite two-dimensional image becomes an image of impression far apart from a two-dimensional image actually acquired by simple imaging. This is a problem similarly occurring in the case of generating a composite two-dimensional image using the minimum value projection method disclosed in JP2014-133095A.

The method disclosed in JP2014-133095A does not reduce the amount of artifacts in the depth direction on the tomographic plane of the subject. For this reason, even if a composite two-dimensional image is generated using the method disclosed in JP2014-133095A, the influence of artifacts in the depth direction cannot be reduced.

In the method disclosed in JP2015-66344A, since it is necessary to generate two kinds of tomographic images, the amount of calculation for generating a composite two-dimensional image increases. Accordingly, a time for processing is required.

The invention has been made in view of the above circumstances, and it is an object of the invention to efficiently generate a composite two-dimensional image, in which the amount of artifacts has been reduced, from a tomographic image acquired by tomosynthesis imaging.

A first image processing apparatus according to the invention comprises: image acquisition unit for acquiring a plurality of projection images corresponding to a plurality of radiation source positions, the plurality of projection images being captured by moving a radiation source relative to detection unit and emitting radiation to a subject at the plurality of radiation source positions due to movement of the radiation source; band tomographic image generation unit for generating a plurality of band tomographic images, which show frequency components of each of a plurality of frequency bands, for each of a plurality of tomographic planes of the subject based on the plurality of projection images; two-dimensional image generation unit for generating a band synthesized two-dimensional image by projecting the plurality of band tomographic images for each of the frequency bands; and frequency synthesizing unit for generating a composite two-dimensional image by weighting the band synthesized two-dimensional image and performing frequency synthesis for each of the frequency bands.

"Move the radiation source relative to the detection unit" includes "move only the radiation source", "move only the detection unit", and "move both the radiation source and the detection unit".

Here, the band synthesized two-dimensional image is a pseudo image, which shows the same image as in the case of acquisition by simple imaging and which is obtained by projecting a different kind of image from a band tomographic image in the same frequency band. As a projection method, a method of simply adding the pixel values of corresponding pixel positions in a plurality of band tomographic images can be mentioned. In addition to the addition, addition averaging for calculating the average value of the added pixel values can also be mentioned as an example. In addition, a maximum value projection method for extracting the maximum value of the corresponding pixel position in a plurality of band tomographic images and a minimum value projection method for extracting the minimum value in a plurality of band tomographic images can also be mentioned.

In the first image processing apparatus according to the invention, the frequency synthesizing unit may generate the composite two-dimensional image by reducing a weighting of a band synthesized two-dimensional image of a low frequency band.

In the first image processing apparatus according to the invention, the frequency synthesizing unit may generate the composite two-dimensional image by reducing a weighting of a band synthesized two-dimensional image from a highest frequency band to a predetermined frequency band.

"From the highest frequency band to the predetermined frequency band" unit not only a plurality of frequency bands including the highest frequency band but also a case where the predetermined frequency band is the highest frequency band, that is, a case of only the highest frequency band.

In the first image processing apparatus according to the invention, the two-dimensional image generation unit may generate the band synthesized two-dimensional image using a different projection method for each of the frequency bands.

In this case, the two-dimensional image generation unit may generate the band synthesized two-dimensional image using a minimum value projection method for a band tomographic image from a highest frequency band to a predetermined frequency band, and generate the band synthesized two-dimensional image using a projection method different from the minimum value projection method for band tomographic images of other frequency bands.

The "minimum value" in the minimum value projection unit a minimum value in a case where the value becomes smaller as the brightness becomes higher, that is, as the density becomes lower. Here, in the projection image, there are a case where the pixel value becomes smaller as the brightness becomes higher and a case where the pixel value becomes larger as the brightness becomes lower. In the latter case, the above-described "minimum value projection" becomes "maximum value projection".

A second image processing apparatus according to the invention comprises: image acquisition unit for acquiring a plurality of projection images corresponding to a plurality of radiation source positions, the plurality of projection images being captured by moving a radiation source relative to detection unit and emitting radiation to a subject at the plurality of radiation source positions due to movement of the radiation source; band tomographic image generation unit for generating a plurality of band tomographic images, which show frequency components of each of a plurality of frequency bands, for each of a plurality of tomographic planes of the subject based on the plurality of projection images; two-dimensional image generation unit for generating a band synthesized two-dimensional image by weighting the plurality of band tomographic images and performing projection for each of the frequency bands; and frequency synthesizing unit for generating a composite two-dimensional image by performing frequency synthesis of the band synthesized two-dimensional image.

In the second image processing apparatus according to the invention, the two-dimensional image generation unit may generate the band synthesized two-dimensional image by reducing a weighting of a band tomographic image of a low frequency band.

In the second image processing apparatus according to the invention, the two-dimensional image generation unit may generate the band synthesized two-dimensional image by reducing a weighting of a band tomographic image from a highest frequency band to a predetermined frequency band.

In the second image processing apparatus according to the invention, the two-dimensional image generation unit may generate the band synthesized two-dimensional image using a different projection method for each of the frequency bands.

In this case, the two-dimensional image generation unit may generate the band synthesized two-dimensional image using a minimum value projection method for a band tomographic image from a highest frequency band to a predetermined frequency band, and generate the band synthesized two-dimensional image using a projection method different from the minimum value projection method for band tomographic images of other frequency bands.

In the second image processing apparatus according to the invention, the two-dimensional image generation unit may generate the band synthesized two-dimensional image by reducing a weighting of a tomographic image at a position away from the radiation source at the time of imaging the subject.

In the first and second image processing apparatuses according to the invention, the two-dimensional image generation unit may generate the band synthesized two-dimensional image by reducing a weighting as a relative movement range of the radiation source with respect to the detection unit decreases.

In the first and second image processing apparatuses according to the invention, the band tomographic image generation unit may comprise: reconstruction unit for generating a plurality of tomographic images on each of the plurality of tomographic planes by reconstructing the plurality of projection images; and frequency decomposition unit for generating the plurality of band tomographic images by frequency-decomposing each of the plurality of tomographic images.

In this case, the frequency decomposition unit may frequency-decompose each of the plurality of tomographic images in a specific direction in the tomographic image.

In the first and second image processing apparatuses according to the invention, the band tomographic image generation unit may comprise: frequency decomposition unit for generating a plurality of band projection images, which show frequency components of each of the plurality of frequency bands, for each of the plurality of projection images by frequency-decomposing each of the plurality of projection images; and reconstruction unit for generating the plurality of band tomographic images by reconstructing the plurality of band projection images for each of the frequency bands.

In this case, the frequency decomposition unit may frequency-decompose each of the plurality of tomographic images in a specific direction in the projection image.

The specific direction may be a direction in which the radiation source is moved relative to the detection unit.

A first image processing method according to the invention comprises: acquiring a plurality of projection images corresponding to a plurality of radiation source positions, the plurality of projection images being captured by moving a radiation source relative to detection unit and emitting radiation to a subject at the plurality of radiation source positions due to movement of the radiation source; generating a plurality of band tomographic images, which show frequency components of each of a plurality of frequency bands, for each of a plurality of tomographic planes of the subject based on the plurality of projection images; generating a band synthesized two-dimensional image by projecting the plurality of band tomographic images for each of the frequency bands; and generating a composite two-dimensional image by weighting the band synthesized two-dimensional image and performing frequency synthesis for each of the frequency bands.

A second image processing method according to the invention comprises: acquiring a plurality of projection images corresponding to a plurality of radiation source positions, the plurality of projection images being captured by moving a radiation source relative to detection unit and emitting radiation to a subject at the plurality of radiation source positions due to movement of the radiation source; generating a plurality of band tomographic images, which show frequency components of each of a plurality of frequency bands, for each of a plurality of tomographic planes of the subject based on the plurality of projection images; generating a band synthesized two-dimensional image by weighting the plurality of band tomographic images and performing projection for each of the frequency bands; and generating a composite two-dimensional image by performing frequency synthesis of the band synthesized two-dimensional image.

In addition, a program causing a computer to execute the first and second image processing methods according to the invention may be provided.

According to the first image processing apparatus, method, and program of the invention, a plurality of band tomographic images, which show frequency components of each of the plurality of frequency bands, for each of the plurality of tomographic planes of the subject are generated based on the plurality of projection images. Then, a band synthesized two-dimensional image is generated by projecting the plurality of band tomographic images for each frequency band, and a composite two-dimensional image is generated by weighting the band synthesized two-dimensional image and performing frequency synthesis for each frequency band. Here, a small structure included in the subject is included in the band synthesized two-dimensional image of a relatively high frequency band, and a relatively large structure is included in the band synthesized two-dimensional image of a relatively low frequency band. As described above, the relatively large structure included in the subject is present over a relatively wide range in the depth direction of the tomographic plane in the subject.

By performing frequency synthesis by weighting the band synthesized two-dimensional image for each frequency band as in the first image processing apparatus, method, and program of the invention, it is possible to generate a composite two-dimensional image in such a manner of reducing the weighting of the band synthesized two-dimensional image of the relatively low frequency band. Accordingly, it is possible to generate a composite two-dimensional image in which the amount of artifacts in the depth direction of a relatively large structure included in the subject has been reduced. In addition, unlike the method disclosed in JP2015-66344A, since it is not necessary to generate two kinds of tomographic images, it is possible to efficiently generate the composite two-dimensional image. In addition, compared with a case of generating a band synthesized two-dimensional image using the maximum value projection method or the minimum value projection method, it is possible to generate a composite two-dimensional image in which thickness information in the subject is reflected and which has an image quality close to a two-dimensional image acquired by simple imaging.

According to the second image processing apparatus, method, and program of the invention, a plurality of band tomographic images, which show frequency components of each of the plurality of frequency bands, for each of the plurality of tomographic planes of the subject are generated based on the plurality of projection images. Then, a band synthesized two-dimensional image is generated by weighting the plurality of band tomographic images and performing projection for each frequency band, and a composite two-dimensional image is generated by performing frequency synthesis of the band synthesized two-dimensional image. Here, a small structure included in the subject is included in the band synthesized two-dimensional image of a relatively high frequency band, and a relatively large structure is included in the band synthesized two-dimensional image of a relatively low frequency band. As described above, the relatively large structure included in the subject is present over a relatively wide range in the depth direction of the tomographic plane in the subject.

As in the second image processing apparatus, method, and program of the invention, by generating the band synthesized two-dimensional image by weighting a plurality of band tomographic images and performing projection, it is possible to generate a band synthesized two-dimensional image in such a manner of reducing the weighting of a band tomographic image of a relatively low frequency band. Accordingly, it is possible to generate a composite two-dimensional image in which the amount of artifacts in the depth direction of a relatively large structure included in the subject has been reduced. In addition, unlike the method disclosed in JP2015-66344A, since it is not necessary to generate two kinds of tomographic images, it is possible to efficiently generate the composite two-dimensional image. In addition, compared with a case of generating a band synthesized two-dimensional image using the maximum value projection method or the minimum value projection method, it is possible to generate a composite two-dimensional image in which thickness information in the subject is reflected and which has an image quality close to a two-dimensional image acquired by simple imaging.

DETAILED DESCRIPTION

Figure 1:
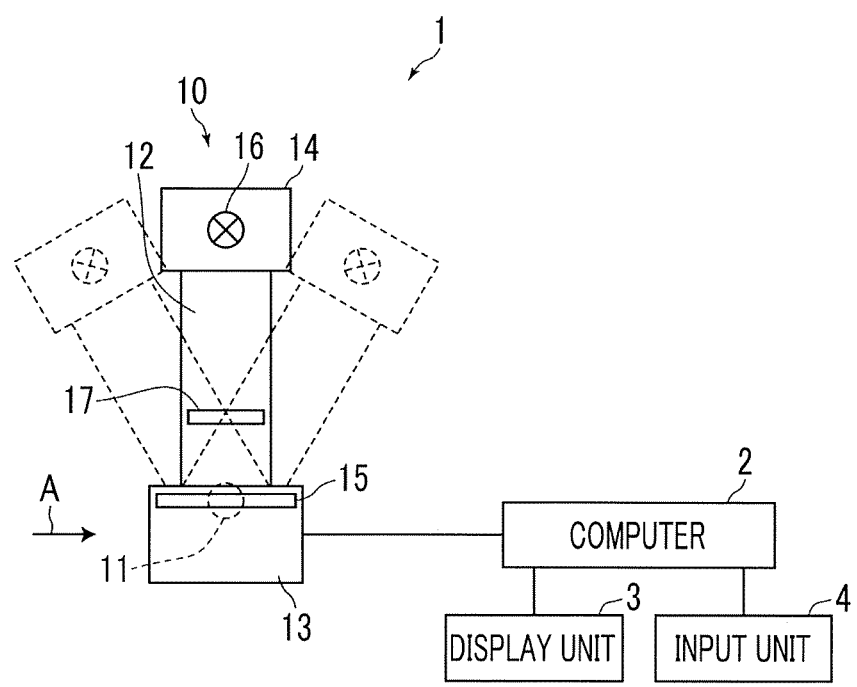
FIG. 1 is a diagram showing the schematic configuration of a radiation image capturing apparatus to which an image processing apparatus according to a first embodiment of the invention is applied.
Figure 2:
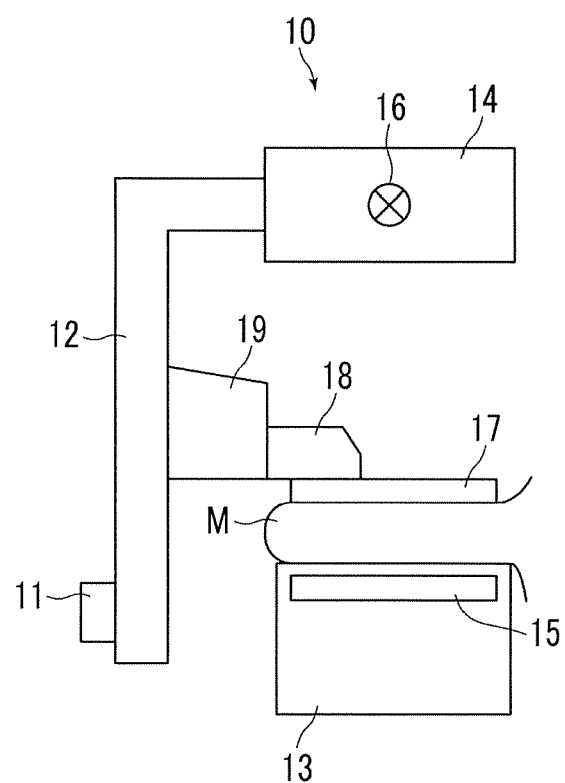
FIG. 2 is a diagram of the radiation image capturing apparatus when viewed from the direction of arrow A in FIG. 1.

Hereinafter, embodiments of the invention will be described with reference to the accompanying diagrams. FIG. 1 is a schematic configuration diagram of a radiation image capturing apparatus to which an image processing apparatus according to a first embodiment of the invention is applied, and FIG. 2 is a diagram of the radiation image capturing apparatus when viewed from the direction of arrow A in FIG. 1. A radiation image capturing apparatus 1 is a mammography imaging apparatus that acquires a plurality of radiation images, that is, projection images, by imaging a breast M (hereinafter, also referred to as a subject M) from a plurality of radiation source positions having different imaging directions in order to generate a tomographic image by performing tomosynthesis imaging of the breast. As shown in FIG. 1, the radiation image capturing apparatus 1 includes an imaging unit 10, a computer 2 connected to the imaging unit 10, and a display unit 3 and an input unit 4 connected to the computer 2.

The imaging unit 10 includes an arm unit 12 connected to a base (not shown) by a rotary shaft 11. An imaging table 13 is attached to one end portion of the arm unit 12, and an irradiation unit 14 is attached to the other end portion so as to face the imaging table 13. The arm unit 12 is configured so as to be able to rotate only the end portion to which the irradiation unit 14 is attached. As a result, only the irradiation unit 14 can be rotated with the imaging table 13 fixed. The rotation of the arm unit 12 is controlled by the computer 2.

A radiation detector 15 (detection unit), such as a flat panel detector, is provided inside the imaging table 13. In addition, a circuit board on which a charge amplifier for converting a charge signal read from the radiation detector 15 into a voltage signal, a sampling two correlation pile circuit for sampling a voltage signal output from the charge amplifier, an AD conversion section for converting a voltage signal into a digital signal, and the like are provided is provided inside the imaging table 13.

The radiation detector 15 can perform recording and reading of a radiation image repeatedly. A so-called direct-type radiation detector that generates an electric charge by direct reception of radiation may be used, or a so-called indirect-type radiation detector that converts radiation into visible light and then converts the visible light into a charge signal may be used. As a method of reading a radiation image signal, it is desirable to use a so-called TFT reading method in which a radiation image signal is read by ON/OFF of a thin film transistor (TFT) switch or a so-called optical reading method in which a radiation image signal is read by emission of reading light. However, other methods may also be used without being limited to the above methods.

An X-ray source 16, which is a radiation source, is housed inside the irradiation unit 14. The timing of emission of X-rays from the X-ray source 16 and X-ray generation conditions in the X-ray source 16, that is, imaging conditions including tube current, time, tube current time product, and the like, are controlled by the computer 2.

A compression plate 17 disposed above the imaging table 13 to compress the breast M, a support unit 18 for supporting the compression plate 17, and a moving mechanism 19 for moving the support unit 18 in the vertical direction in FIGS. 1 and 2 are provided in the arm unit 12.

The display unit 3 is a display device, such as a CRT or a liquid crystal monitor, and displays a projection image acquired as will be described later, a generated tomographic image, a message required for the operation, and the like. The display unit 3 may include a speaker that outputs sound.

The input unit 4 is a keyboard, a mouse, or a touch panel type input device, and receives an operation of the radiation image capturing apparatus 1 by the operator. In addition, the input unit 4 receives an input of various kinds of information, such as imaging conditions, and an instruction to modify information, which are required to perform tomosynthesis imaging. In the present embodiment, each unit of the radiation image capturing apparatus 1 operates according to the information input from the input unit 4 by the operator.

An image processing program according to the first embodiment is installed in the computer 2. In the present embodiment, the computer 2 may be a workstation or a personal computer that is directly operated by the operator, or may be a server computer connected to these through a network. The image processing program is distributed by being recorded on a recording medium, such as a digital versatile disc (DVD) and a compact disc read only memory (CD-ROM), and is installed into the computer from the recording medium. Alternatively, the image processing program is stored in a storage device of a server computer connected to the network or in a network storage so as to be accessible from the outside, and is downloaded and installed into the computer when necessary.

Figure 3:
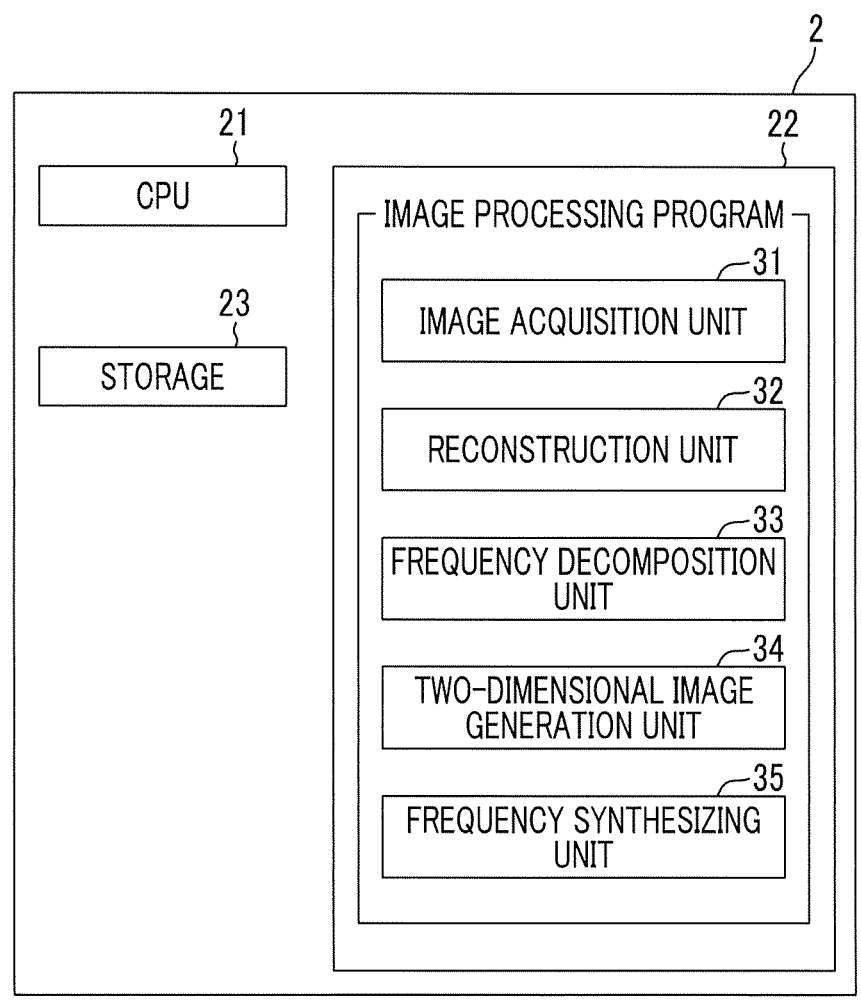
FIG. 3 is a diagram showing the schematic configuration of an image processing apparatus realized by installing an image processing program in a computer in the first embodiment.

FIG. 3 is a diagram showing the schematic configuration of an image processing apparatus realized by installing an image processing program in the computer 2. As shown in FIG. 3, the image processing apparatus includes a central processing unit (CPU) 21, a memory 22, and a storage 23 as the configuration of a standard computer.

The storage 23 is a storage device, such as a hard disk or a solid state drive (SSD), and stores various kinds of information including a program for driving each unit of the radiation image capturing apparatus 1 and an image processing program. In addition, a projection image acquired by tomosynthesis imaging, a tomographic image generated as will be described later, and the like are stored.

The memory 22 temporarily stores programs and the like stored in the storage 23 so that the CPU 21 execute various kinds of processing. As processing to be executed by the CPU 21, the image processing program specifies: image acquisition processing for acquiring a plurality of projection images of the breast M by causing the radiation image capturing apparatus 1 to perform tomosynthesis imaging; reconstruction processing for reconstructing the plurality of projection images to generate a plurality of tomographic images on a plurality of tomographic planes of the breast M; frequency decomposition processing for performing frequency decomposition on each of the plurality of tomographic images to generate a plurality of band tomographic images, which show frequency components of each of a plurality of frequency bands, for each of the plurality of tomographic images; two-dimensional image generation processing for generating a band synthesized two-dimensional image by projecting the plurality of band tomographic images for each frequency band; and frequency synthesis processing for generating a composite two-dimensional image by weighting a band synthesized two-dimensional image and performing frequency synthesis for each frequency band.

The CPU 21 executes these processes according to the image processing program, so that the computer 2 functions as an image acquisition unit 31, a reconstruction unit 32, a frequency decomposition unit 33, a two-dimensional image generation unit 34, and a frequency synthesizing unit 35. The computer 2 may include a processor or a processing circuit that performs image acquisition processing, reconstruction processing, frequency decomposition processing, two-dimensional image generation processing, and frequency synthesis processing. The reconstruction unit 32 and the frequency decomposition unit 33 form band tomographic image generation unit of the invention.

Figure 4:
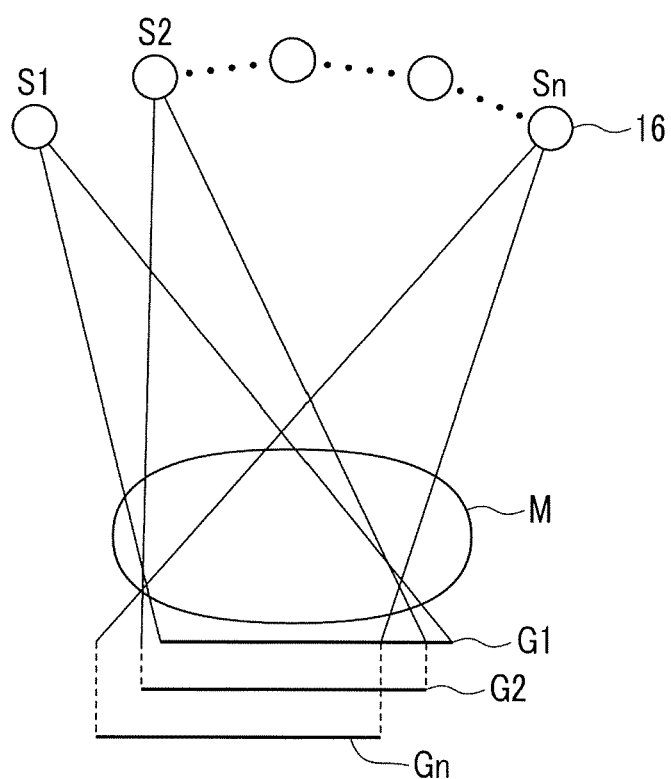
FIG. 4 is a diagram illustrating the acquisition of a projection image.

By rotating the arm unit 12 around the rotary shaft 11 to move the X-ray source 16 within a predetermined angle range (for example, ±15° with respect to an axis perpendicular to the detection surface of the radiation detector 15), X-rays are emitted to the breast M that is a subject at a plurality of radiation source positions according to the movement of the X-ray source 16. X-rays transmitted through the breast M are detected by the radiation detector 15. Accordingly, the image acquisition unit 31 acquires a plurality of projection images Gi (i=1 to n, where n is the number of radiation source positions) at a plurality of radiation source positions. FIG. 4 is a diagram illustrating the acquisition of the projection image Gi. As shown in FIG. 4, the X-ray source 16 is moved to each radiation source position of S1, S2, . . . , Sn, the X-ray source 16 is driven at each radiation source position to irradiate the breast M with X-rays, and the X-rays transmitted through the breast M is detected by the radiation detector 15. As a result, projection images G1, G2, . . . , Gn are acquired corresponding to the radiation source positions S1 to Sn. The plurality of acquired projection images Gi are stored in the storage 23. The plurality of projection images Gi may be acquired by a program separate from the image processing program, and be stored in the storage 23. In this case, the image acquisition unit 31 reads the plurality of projection images Gi stored in the storage 23 from the storage 23 for reconstruction processing or the like.

In the present embodiment, all of the plurality of projection images Gi stored in the storage 23 may be read and used for reconstruction processing or the like, or two or more predetermined number of projection images Gi among the plurality of projection images Gi may be read and used for reconstruction processing or the like.

The reconstruction unit 32 generates tomographic images on a plurality of tomographic planes of the breast M by reconstructing the plurality of projection images Gi. Specifically, the reconstruction unit 32 generates a tomographic image TGj on each of a plurality of tomographic planes Tj (j=1 to m: m is the number of tomographic planes) by reconstructing the projection image Gi using a known back projection method, such as a simple back projection method or a filtered back projection method, a shift addition method, or the like. Here, it is assumed that the tomographic planes Tj are aligned as T1, T2, . . . in order from the tomographic plane closest to the X-ray source 16 in the breast M.

As a reconstruction method, in addition to the back projection method and the shift addition method, a known CT reconstruction method (as an example, the FBP method described above) can be used. The FBP method is a reconstruction method as an extended version of the filtered back projection method, in which parallel plane type tomographic scanning of tomography is regarded as a part of a cone beam CT scan. As a reconstruction method, an iterative reconstruction method disclosed in JP2011-125698A can also be used. The iterative reconstruction method is a reconstruction method for CT, but can also be applied to reconstruction at the time of tomosynthesis imaging as the FBP method.

Figure 5:
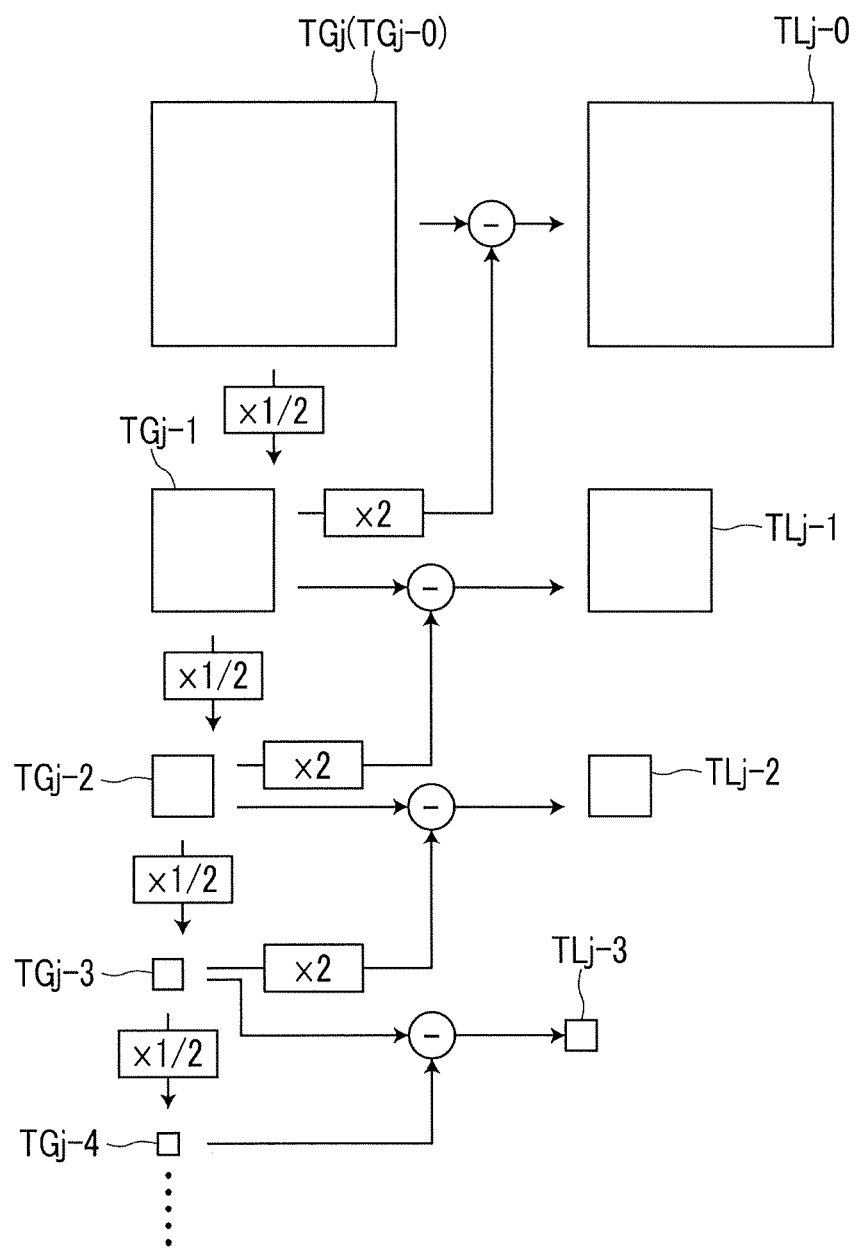
FIG. 5 is a diagram illustrating frequency decomposition in the first embodiment.

The frequency decomposition unit 33 frequency-decomposes each of the plurality of tomographic images TGj to generate a plurality of band tomographic images, which show frequency components of each of the plurality of frequency bands, for each of the plurality of tomographic images TGj. FIG. 5 is a diagram illustrating frequency decomposition performed by the frequency decomposition unit 33. First, the frequency decomposition unit 33 performs filtering processing on the tomographic image TGj of a certain frequency band with, for example, a Gaussian filter of σ=1 to minify the tomographic image TGj to ½, thereby generating a minified tomographic image TGj-1 that is a Gaussian component. The minified tomographic image TGj-1 is obtained by minifying the tomographic image TGj to ½. In the following description, the tomographic image TGj may be referred to as a tomographic image TGj-0 for convenience. Then, the frequency decomposition unit 42 performs an interpolation operation, such as cubic B-spline interpolation, to enlarge the minified tomographic image TGj-1 twice so as to have the same size as the tomographic image TGj-0, and subtracts the enlarged minified tomographic image TGj-1 from the tomographic image TGj-0, thereby generating a band tomographic image TLj-0 that is a Laplacian component of the highest frequency band. In the present embodiment, the highest frequency band is referred to as a 0-th frequency band for convenience.

Then, the frequency decomposition unit 33 performs filtering processing on the minified tomographic image TGj-1 with a Gaussian filter of σ=1 to minify the minified tomographic image TGj-1 to ½, thereby generating a minified tomographic image TGj-2. Then, the frequency decomposition unit 33 enlarges the minified tomographic image TGj-2 twice so as to have the same size as the minified tomographic image TGj-1, and subtracts the enlarged minified tomographic image TGj-2 from the minified tomographic image TGj-1, thereby generating a band tomographic image TLj-1 of the first frequency band. By repeating the above-described processing until a band projection image of a desired frequency band is generated, a band tomographic image TLj-k (k=0 to a: a is the number of bands) of a plurality of frequency bands is generated. In the present embodiment, assuming that a is 10, the above-described processing is repeated until a band tomographic image TLj-10 of the tenth frequency band is obtained.

Here, the signal value of each pixel of the minified tomographic image indicates the density of the pixel, and the signal value of each pixel of the band tomographic image TLj-k indicates the magnitude of the frequency component of the frequency band in the pixel. A plurality of band tomographic images TLj-k having different frequency bands may be generated by using other methods of multi-resolution conversion, such as wavelet transformation.

Figure 6:
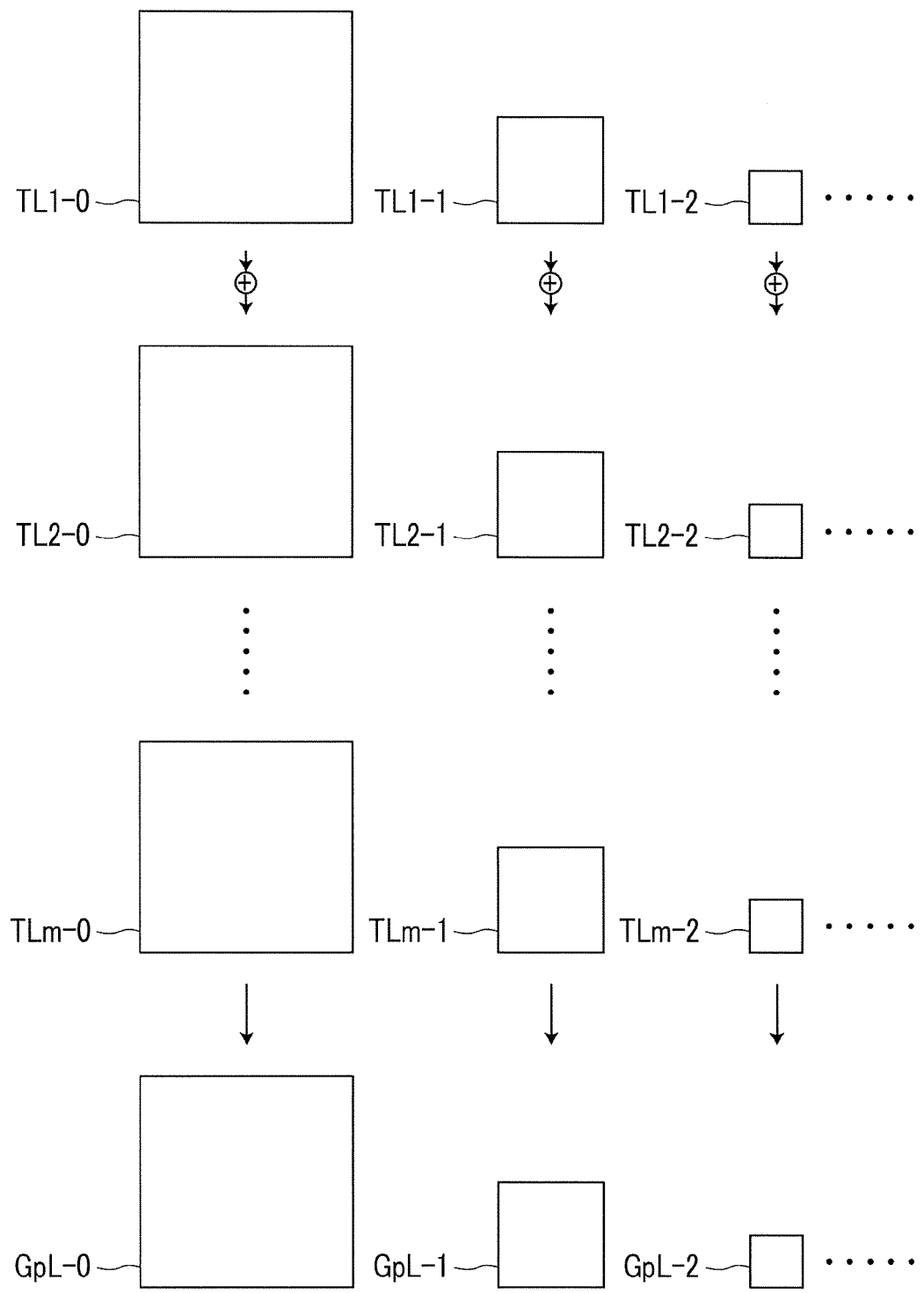
FIG. 6 is a diagram illustrating the generation of a band synthesized two-dimensional image in the first embodiment.

The two-dimensional image generation unit 34 generates a band synthesized two-dimensional image GpL-k by projecting a plurality of band tomographic images TLj-k for each frequency band. FIG. 6 is a diagram illustrating the generation of a band synthesized two-dimensional image in the first embodiment. As shown in FIG. 6, the two-dimensional image generation unit 34 generates the band synthesized two-dimensional image GpL-k by performing projection processing on a plurality of band tomographic images TLj-k along a predetermined direction. In the present embodiment, the predetermined direction is a direction perpendicular to the tomographic plane Tj. In the present embodiment, as the projection processing, addition processing for adding corresponding pixel values along a predetermined direction is used. For example, in the highest frequency band, by adding the corresponding pixel values of band tomographic images TL1-0, TL2-0, . . . , TLm-0 generated on all the tomographic planes Tj, a band synthesized two-dimensional image GpL-0 of the highest frequency band is generated. In a frequency band next to the highest frequency band, by adding the corresponding pixel values of band tomographic images TL1-1, TL2-1, . . . , TLm-1 generated on all the tomographic planes Tj, a band synthesized two-dimensional image GpL-1 of the highest frequency band is generated. The band synthesized two-dimensional image GpL-k may be generated by performing not only simple addition but also addition averaging that is to divide the addition value by the number of tomographic planes Tj.

The frequency synthesizing unit 35 performs frequency synthesis by weighting the band synthesized two-dimensional image GpL-k for each frequency band, thereby generating a composite two-dimensional image Gp. Hereinafter, weighting in the first embodiment will be described.

Figure 7:
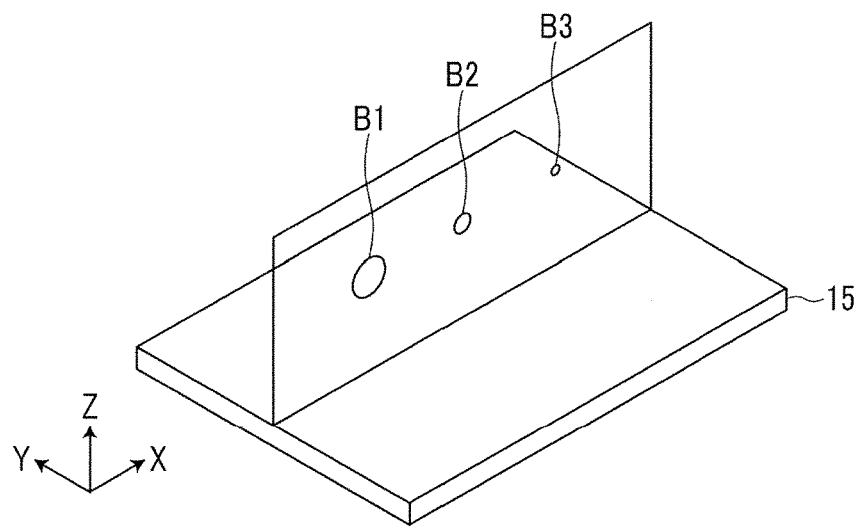
FIG. 7 is a diagram schematically showing an example of tomosynthesis imaging.

FIG. 7 is a diagram schematically showing an example of tomosynthesis imaging. The Z axis in FIG. 7 indicates a coordinate value (distance from the detection surface) in a direction perpendicular to the detection surface of the radiation detector 15. The detection surface of the radiation detector 15 is a plane of Z=0. The movement direction of the X-ray source 16, that is, the left and right direction of the paper surface in FIG. 1 is set as an X-axis direction, and a direction perpendicular to the paper surface of FIG. 1 is set as a Y-axis direction. In addition, a Z-axis direction is a vertical direction in FIG. 1. In FIG. 7, it is assumed that three spherical structures B1 to B3 are arranged in the X-axis direction in parallel to the detection surface of the radiation detector 15, on the XZ cross section on the X axis, so that the Z coordinates of the center positions of the three spherical structures B1 to B3 have the same value. Among the three structures, the size of the structure B1 is the largest, and the size of the structure B3 is the smallest.

Figure 8:
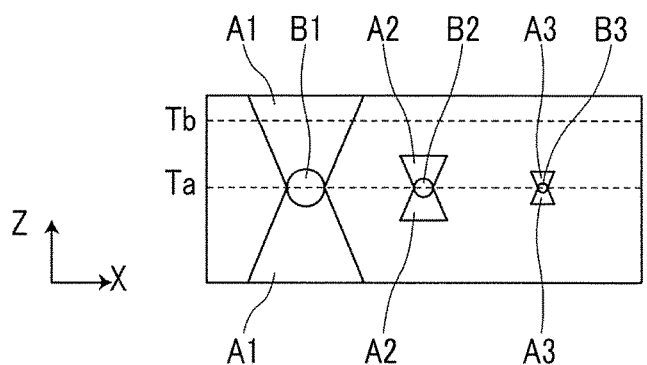
FIG. 8 is a diagram illustrating the generation of artifacts in the depth direction.
Figure 9:
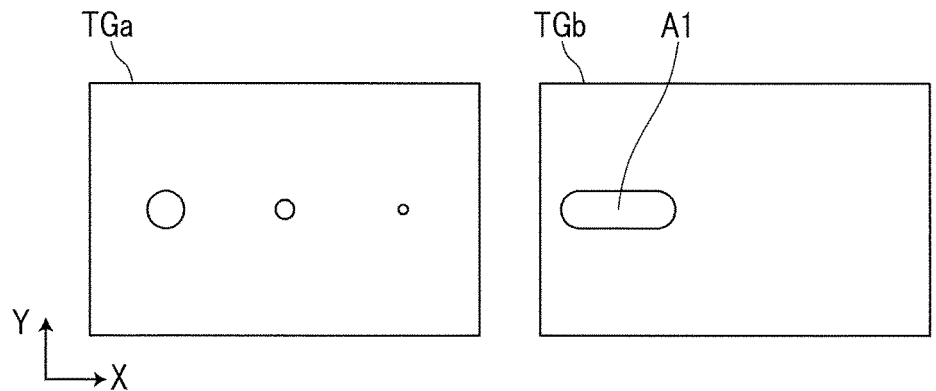
FIG. 9 is a diagram showing tomographic images corresponding to tomographic planes Ta and Tb in FIG. 8.

FIG. 8 is a diagram illustrating the generation of artifacts in the depth direction. FIG. 8 shows a cross-sectional view parallel to the X-Z plane when the reconstructed tomographic image TGj generated from a projection image acquired by tomosynthesis imaging of a subject including the three structures B1 to B3 shown in FIG. 7 is laminated in the depth direction (that is, in the Z-axis direction) of the breast M so as to correspond to the tomographic plane Tj of each tomographic image. FIG. 9 shows tomographic images TGa and TGb corresponding to tomographic planes Ta and Tb in FIG. 8.

As shown in FIG. 8 and FIG. 9, the tomographic plane Ta corresponds to a position where the three structures B1 to B3 are actually present, and images of the three structures B1 to B3 clearly appear in the tomographic image TGa of the tomographic plane Ta. However, although the tomographic plane Tb is a position where the structure B1 is not present originally, an artifact A1 of the structure B1 is reflected in the tomographic image TGb of the tomographic plane Tb.

Figure 10:
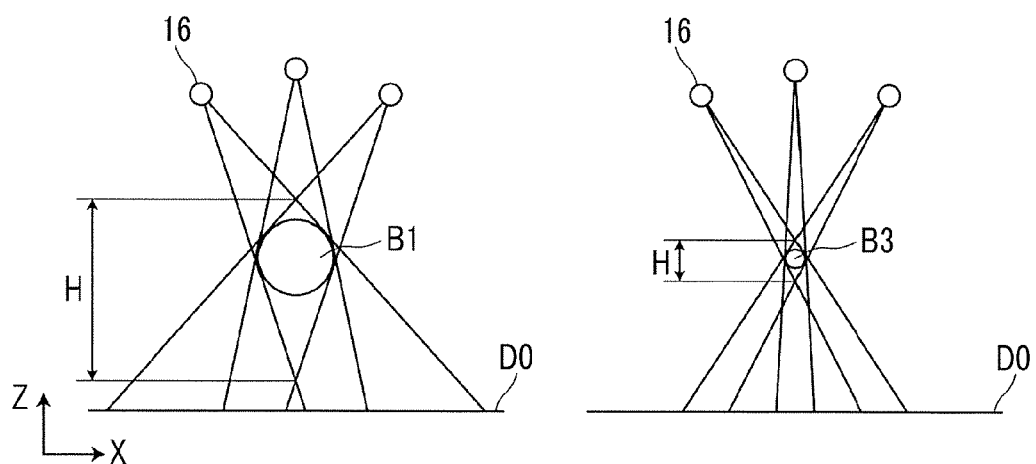
FIG. 10 is a diagram illustrating the relationship between the size of a structure and an artifact in the depth direction.

FIG. 10 is a diagram illustrating the relationship between the size of a structure and an artifact in the depth direction. As shown in FIG. 10, when the structure is irradiated with X-rays from the X-ray source 16 at a plurality of positions, an artifact by which the structure extends in the depth direction as shown in FIG. 8 is generated in a range H in the depth direction (Z-axis direction) where X-ray irradiation regions overlap each other. When the structures B1 and B3 are compared, as the size of the structure increases, the X-ray irradiation area increases, X-rays transmitted through the structure are detected on the detection surface D0, and the size thereof reflected in the projection image increases. As a result, the range H where artifacts in the depth direction are generated increases. That is, as shown in FIG. 8, when the artifacts A1 to A3 of the structures B1 to B3 are compared, the range of the artifact A1 of the largest structure B1 in the depth direction is the largest.

Figure 11:
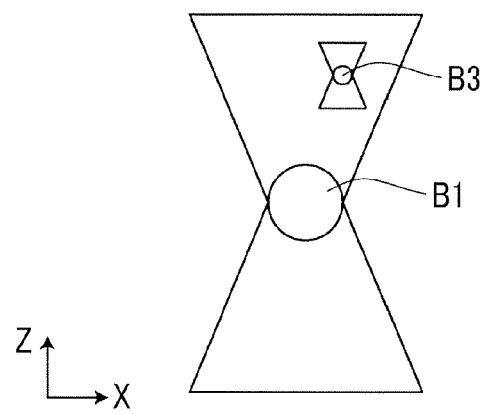
FIG. 11 is a diagram illustrating the influence of artifacts of a large structure.

For this reason, as shown in FIG. 11, in a case where the large structure B1 and the small structure B3 are present side by side in the Z-axis direction on the same X-Z plane, the image of the structure B3 disappears in the tomographic image of the tomographic plane where the structure B3 is present due to the influence of the artifact A1 in the depth direction of the structure B1. As a result, when a composite two-dimensional image is generated by adding the corresponding pixel positions of the respective tomographic images, it is not possible to see the small structure B3 in the composite two-dimensional image due to the influence of the artifact A1 in the depth direction of the large structure B1.

Here, when the tomographic image is subjected to frequency decomposition, the large structure is included in a band tomographic image of a low frequency band, and the small (minute) structure is included in a band tomographic image of a high frequency band. Artifacts in the depth direction caused by the large structure are included in a larger number of tomographic images compared with artifacts caused by the small structure. Accordingly, many artifacts caused by the large structure are included in the band tomographic image of the low frequency band.

In the first embodiment, the frequency synthesizing unit 35 reduces the weighting of the band synthesized two-dimensional image GpL-k of the low frequency band, and performs frequency synthesis of the band synthesized two-dimensional image GpL-k to generate the composite two-dimensional image Gp. Here, assuming that the weighting coefficient for the band synthesized two-dimensional image GpL-k of each frequency band is Wk, the frequency synthesizing unit 35 reduces the value of the weighting coefficient Wk ask increases, that is, as the frequency band becomes low. Specifically, although the weighting coefficient Wk depends on the size of a structure, such as a lesion included in the breast M, the weighting coefficient Wk for the band synthesized two-dimensional image GpL-k from the highest frequency band to a predetermined frequency band is set to 1, and the weighting coefficient Wk is set so as to become gradually smaller than 1 as the frequency band becomes lower. For example, in the case of k=10, the weighting coefficient W10 for the band synthesized two-dimensional image GpL-10 of the lowest frequency band may be set to 1/10.

Figure 12:
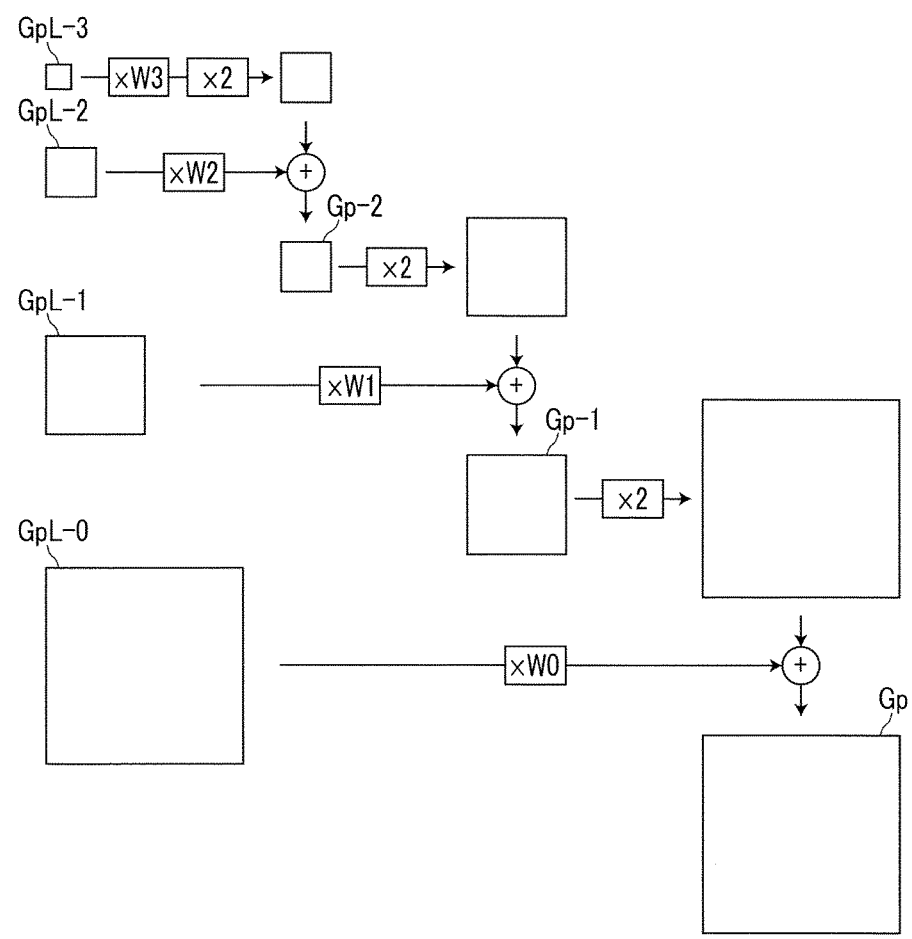
FIG. 12 is a diagram illustrating frequency synthesis in the first embodiment.

FIG. 12 is a diagram illustrating frequency synthesis in the first embodiment. In the present embodiment, band synthesized two-dimensional images up to the band synthesized two-dimensional image GpL-10 of the tenth frequency band are generated. However, in order to simplify the explanation, it is assumed that frequency synthesis is performed from the band synthesized two-dimensional image GpL-3 of the third frequency band.

The frequency synthesizing unit 35 multiplies the band synthesized two-dimensional image GpL-3 of the third frequency band by the weighting coefficient W3, and doubles the size of the band synthesized two-dimensional image GpL-3 of the third frequency band multiplied by the weighting coefficient W3 by performing an interpolation operation. Then, the frequency synthesizing unit 35 multiplies the band synthesized two-dimensional image GpL-2 of the second frequency band by the weighting coefficient W2, and adds up the weighted band synthesized two-dimensional image GpL-2 of the second frequency band and the band synthesized two-dimensional image GpL-3 of the third frequency band to generate a composite two-dimensional image Gp-2. Then, the frequency synthesizing unit 35 enlarges the composite two-dimensional image Gp-2 twice, and adds up the enlarged composite two-dimensional image Gp-2 and the band synthesized two-dimensional image GpL-1 of the first frequency band multiplied by the weighting coefficient W1 to generate a composite two-dimensional image Gp-1. Then, the frequency synthesizing unit 35 enlarges the composite two-dimensional image Gp-1 twice, and adds up the enlarged composite two-dimensional image Gp-1 and the band synthesized two-dimensional image GpL-0 of the 0-th frequency band multiplied by the weighting coefficient W0 to generate a composite two-dimensional image Gp-0, that is, a composite two-dimensional image Gp.

Figure 13:
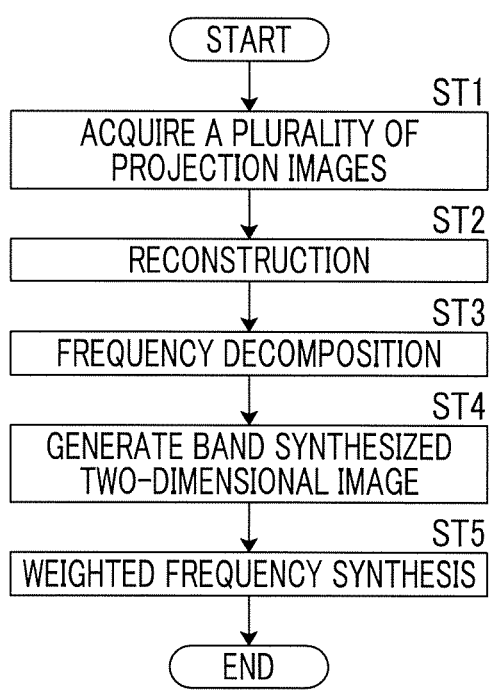
FIG. 13 is a flowchart showing the process performed in the first embodiment.

Next, the process performed in the first embodiment will be described. FIG. 13 is a flowchart showing the process performed in the first embodiment. When the input unit 4 receives an operator's instruction to start the process, tomosynthesis imaging is performed and the image acquisition unit 31 acquires a plurality of projection images Gi (step ST1). Then, the reconstruction unit 32 reconstructs the plurality of projection images Gi to generate a plurality of tomographic images TGj on a plurality of tomographic planes Tj (step ST2). Then, the frequency decomposition unit 33 frequency-decomposes each of the plurality of tomographic images TGj to generate a plurality of band tomographic images TLi-k, which show frequency components of each of the plurality of frequency bands, for each of the plurality of tomographic images TGj (step ST3).

Then, the two-dimensional image generation unit 34 generates the band synthesized two-dimensional image GpL-k by projecting the plurality of band tomographic image TLj-k for each frequency band (step ST4). Then, the frequency synthesizing unit 35 performs frequency synthesis by weighting the band synthesized two-dimensional image GpL-k for each frequency band, thereby generating the composite two-dimensional image Gp (weighted frequency synthesis: step ST5). Then, the process is ended.

Here, a small structure included in the subject is included in the band synthesized two-dimensional image of a relatively high frequency band, and a relatively large structure is included in the band synthesized two-dimensional image of a relatively low frequency band. As described above, the relatively large structure included in the subject is present over a relatively wide range in the depth direction of the tomographic plane in the subject M. By performing frequency synthesis by weighting the band synthesized two-dimensional image for each frequency band as in the first embodiment, it is possible to generate the composite two-dimensional image Gp in such a manner of reducing the weighting of the band synthesized two-dimensional image of the relatively low frequency band. Accordingly, it is possible to generate the composite two-dimensional image Gp in which the amount of artifacts in the depth direction of the relatively large structure included in the subject M has been reduced. In addition, unlike the method disclosed in JP2015-66344A, since it is not necessary to generate two kinds of tomographic images, it is possible to efficiently generate the composite two-dimensional image Gp. In addition, compared with a case of generating a band synthesized two-dimensional image using the maximum value projection method or the minimum value projection method, it is possible to generate the composite two-dimensional image Gp in which thickness information in the subject M is reflected and which has an image quality close to a two-dimensional image acquired by simple imaging.

Next, a second embodiment of the invention will be described. An image processing apparatus according to the second embodiment has the same configuration as the image processing apparatus according to the first embodiment, and only the processing to be performed is different. Accordingly, the detailed explanation of the apparatus will be omitted herein. In the first embodiment described above, the two-dimensional image generation unit 34 generates the band synthesized two-dimensional image GpL-k, and the frequency synthesizing unit 35 generates the composite two-dimensional image Gp by weighting the band synthesized two-dimensional image GpL-k and performing frequency synthesis for each frequency band. The second embodiment is different from the first embodiment in that the two-dimensional image generation unit 34 generates a band synthesized two-dimensional image W0-k·GpL-k by weighting a plurality of band tomographic images TLj-k and performing projection for each frequency band and that the frequency synthesizing unit 35 generates the composite two-dimensional image Gp by performing frequency synthesis of the weighted band synthesized two-dimensional image W0-k·GpL-k.

In the second embodiment, the two-dimensional image generation unit 34 multiplies each of the plurality of band tomographic images TLj-k by a weighting coefficient W0-k for each frequency band. Here, in the first embodiment described above, the composite two-dimensional image Gp is generated by multiplying the band synthesized two-dimensional image GpL-k by the weighting coefficient Wk. (k+1) band synthesized two-dimensional images GpL-k are generated. Therefore, the weighting coefficient W0-k used in the second embodiment is a value obtained by dividing the weighting coefficient Wk for the same frequency band in the first embodiment by (k+1).

Figure 14:
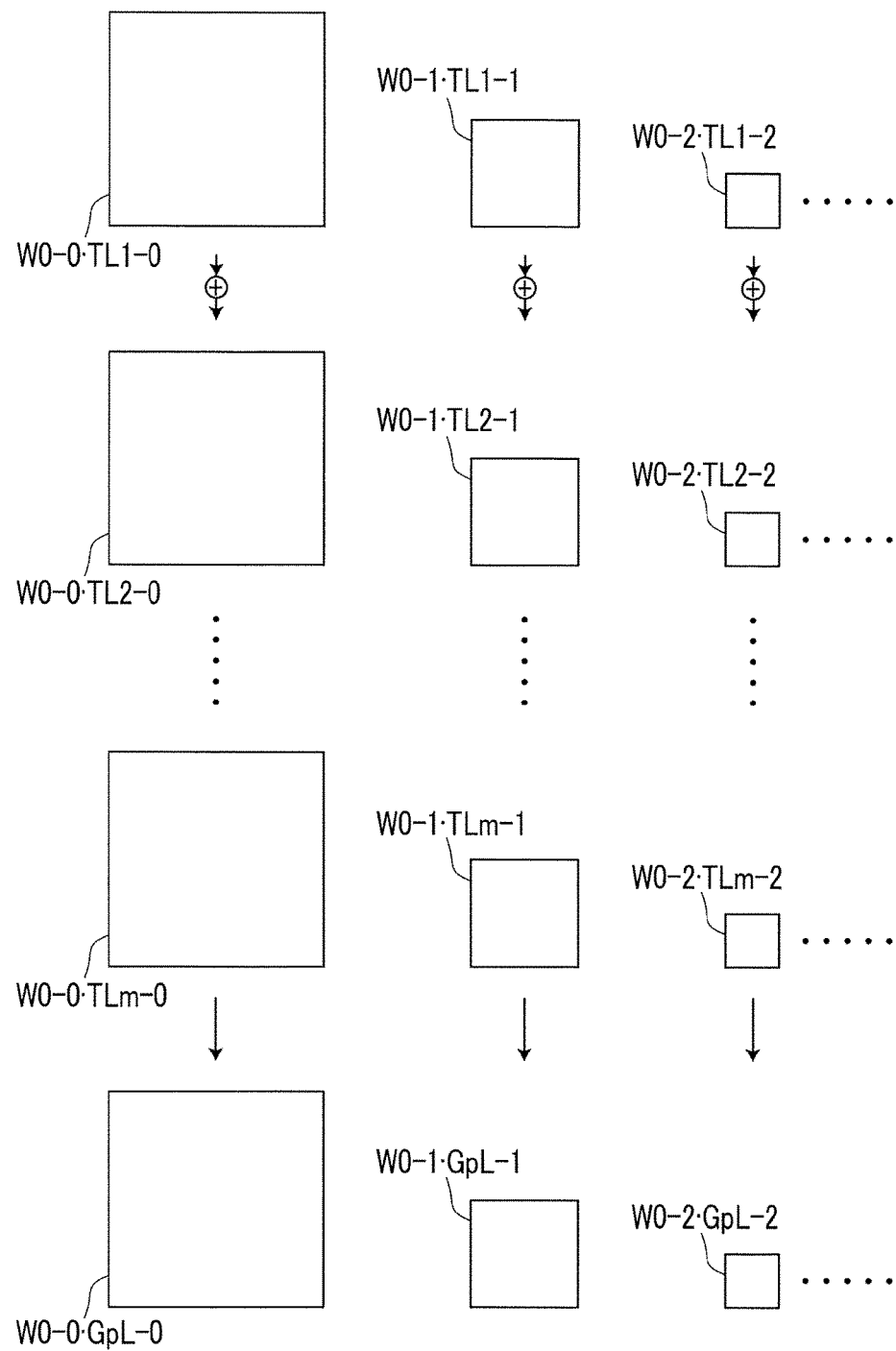
FIG. 14 is a diagram illustrating the generation of a band synthesized two-dimensional image in a second embodiment.

FIG. 14 is a diagram illustrating the generation of a band synthesized two-dimensional image in the second embodiment. As shown in FIG. 14, the two-dimensional image generation unit 34 multiplies each of the plurality of band tomographic images TLj-k by the weighting coefficient W0-k, and performs projection processing on a plurality of band tomographic images W0-k·TLj-k multiplied by the weighting coefficient W0-k along a predetermined direction, thereby generating the band synthesized two-dimensional image W0-k·GpL-k. Also in the second embodiment, the predetermined direction is a direction perpendicular to the tomographic plane Tj. In addition, also in the second embodiment, as the projection processing, addition processing for adding corresponding pixel values along a predetermined direction is used. Instead of multiplying each of the plurality of band tomographic images TLj-k by the weighting coefficient W0-k, the band synthesized two-dimensional image GpL-k may be generated in the same manner as in the first embodiment, and the two-dimensional image generation unit 34 may multiply the band synthesized two-dimensional image GpL-k by the same weighting coefficient Wk as in the first embodiment.

The frequency synthesizing unit 35 performs frequency synthesis of the band synthesized two-dimensional image W0-k·GpL-k to generate the composite two-dimensional image Gp.

Figure 15:
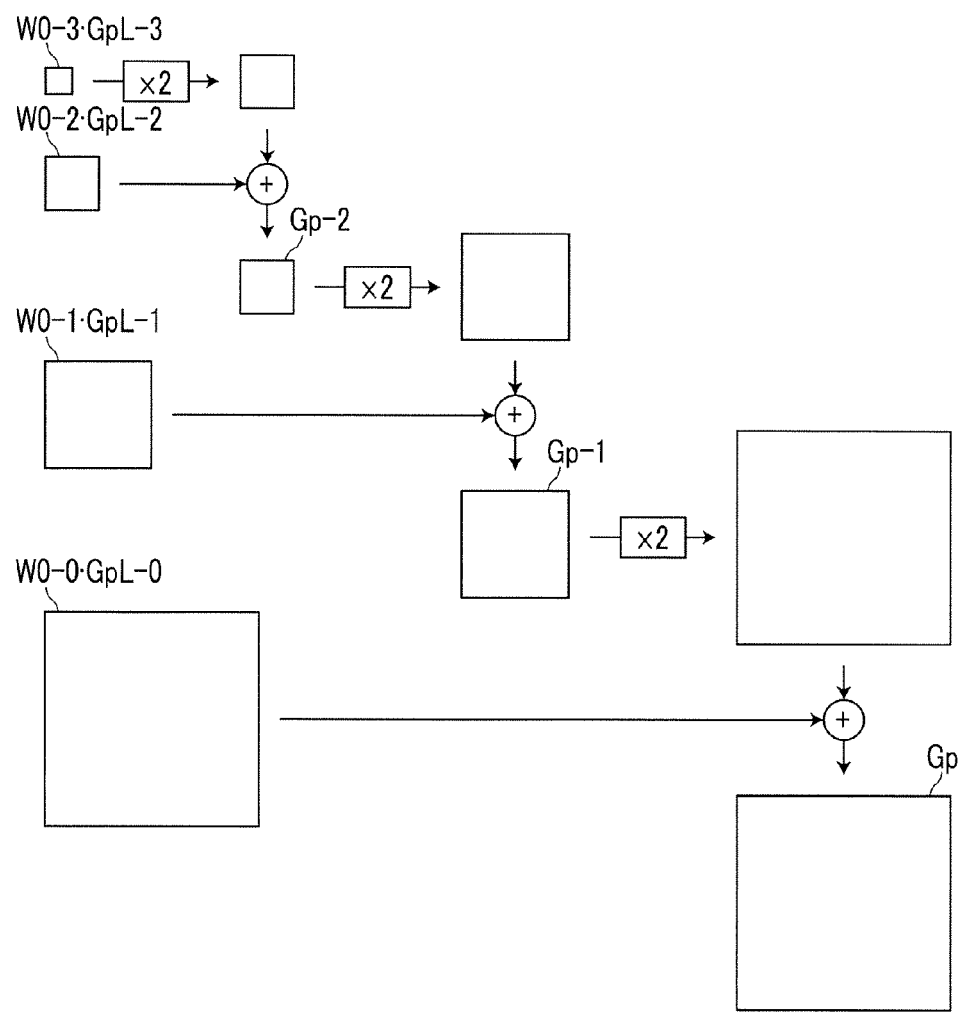
FIG. 15 is a diagram illustrating frequency synthesis in the second embodiment.

FIG. 15 is a diagram illustrating frequency synthesis in the second embodiment. In the second embodiment, band synthesized two-dimensional images up to the band synthesized two-dimensional image GpL-10 of the tenth frequency band are generated. However, in order to simplify the explanation, it is assumed that frequency synthesis is performed from the band synthesized two-dimensional image W0-3·GpL-3 of the third frequency band.

In the second embodiment, the frequency synthesizing unit 35 enlarges the band synthesized two-dimensional image W0-3·GpL-3 of the third frequency band twice by interpolation operation, and adds up the enlarged band synthesized two-dimensional image W0-3·GpL-3 of the third frequency band and the band synthesized two-dimensional image W0-2·GpL-2 of the second frequency band to generate a composite two-dimensional image Gp-2. Then, the frequency synthesizing unit 35 enlarges the composite two-dimensional image Gp-2 twice, and adds up the enlarged composite two-dimensional image Gp-2 and the band synthesized two-dimensional image W0-1·GpL-1 of the first frequency band to generate a composite two-dimensional image Gp-1. Then, the frequency synthesizing unit 35 enlarges the composite two-dimensional image Gp-1 twice, and adds up the enlarged composite two-dimensional image Gp-1 and the band synthesized two-dimensional image W0-0·GpL-0 of the 0-th frequency band to generate a composite two-dimensional image Gp-0, that is, a composite two-dimensional image Gp.

Figure 16:
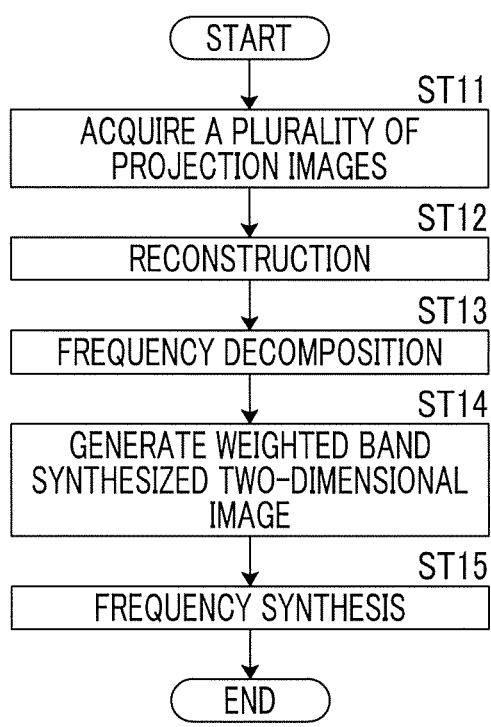
FIG. 16 is a flowchart showing the process performed in the second embodiment.

Next, the process performed in the second embodiment will be described. FIG. 16 is a flowchart showing the process performed in the second embodiment. When the input unit 4 receives an operator's instruction to start the process, tomosynthesis imaging is performed and the image acquisition unit 31 acquires a plurality of projection images Gi (step ST11). Then, the reconstruction unit 32 reconstructs the plurality of projection images Gi to generate a plurality of tomographic images TGj on a plurality of tomographic planes Tj (step ST12). Then, the frequency decomposition unit 33 frequency-decomposes each of the plurality of tomographic images TGj to generate a plurality of band tomographic images TLi-k, which show frequency components of each of the plurality of frequency bands, for each of the plurality of tomographic images TGj (step ST13).

Then, the two-dimensional image generation unit 34 generates the band synthesized two-dimensional image W0-k·GpL-k by weighting the plurality of band tomographic images TGj-k and performing projection for each frequency band (weighted band synthesized two-dimensional image generation: step ST14). Then, the frequency synthesizing unit 35 performs frequency synthesis of the band synthesized two-dimensional image W0-k·GpL-k to generate the composite two-dimensional image Gp (step ST15). Then, the process is ended.

As described above, in the second embodiment, since a band synthesized two-dimensional image is generated by weighting a plurality of band tomographic images and performing projection, it is possible to generate a band synthesized two-dimensional image in such a manner of reducing the weighting of a band tomographic image of a relatively low frequency band. Accordingly, it is possible to generate the composite two-dimensional image Gp in which the amount of artifacts in the depth direction of a relatively large structure included in the subject M has been reduced. In addition, unlike the method disclosed in JP2015-66344A, since it is not necessary to generate two kinds of tomographic images, it is possible to efficiently generate the composite two-dimensional image Gp. In addition, compared with a case of generating a band synthesized two-dimensional image using the maximum value projection method or the minimum value projection method, it is possible to generate the composite two-dimensional image Gp in which thickness information in the subject M is reflected and which has an image quality close to a two-dimensional image acquired by simple imaging.

Next, a third embodiment of the invention will be described. An image processing apparatus according to the third embodiment has the same configuration as the image processing apparatus according to the first embodiment, and only the processing to be performed is different. Accordingly, the detailed explanation of the apparatus will be omitted herein. Here, artifacts in the depth direction due to the size of a structure are included in a radiation image as low frequency components. Therefore, in the first embodiment described above, the frequency synthesizing unit 35 generates the composite two-dimensional image Gp by reducing the weighting of the band synthesized two-dimensional image GpL-k of the low frequency band.

On the other hand, in the band synthesized two-dimensional image GpL-k of the highest frequency band and a frequency band close thereto, a noise component may be dominant. The third embodiment is different from the first embodiment in that the composite two-dimensional image Gp is generated by reducing the weighting for the band synthesized two-dimensional image from the highest frequency band to a predetermined frequency band as well.

In the third embodiment, in the processing shown in FIG. 12, the weighting coefficient W0 for the band synthesized two-dimensional image GpL-0 of the highest frequency band is set to 0, so that the component of the band synthesized two-dimensional image GpL-0 of the highest frequency band is not included in the composite two-dimensional image Gp. A weighting coefficient larger than 0 may be used as long as the weighting coefficient is a relatively low value. In addition, the weighting coefficient Wk for the band synthesized two-dimensional image GpL-k of a plurality of frequency bands that can be regarded as noise, such as not only the highest frequency band but also a frequency band next to the highest frequency band or even the next frequency band, may be reduced.

In this manner, by generating the composite two-dimensional image Gp by reducing the weighting of the band synthesized two-dimensional image from the highest frequency band to the predetermined frequency band, it is possible to generate the composite two-dimensional image Gp with higher image quality and reduced noise.

In the second embodiment described above, the band synthesized two-dimensional image GpL-k may be generated by reducing the weighting of the band tomographic image TL-k from the highest frequency band to the predetermined frequency band. For example, in the processing shown in FIG. 14, the weighting coefficient W0-$k$ for the band tomographic image TLj-0 of the highest frequency band is set to 0, so that the two-dimensional image generation unit 34 does not generate the band synthesized two-dimensional image GpL-0 of the highest frequency band. A weighting coefficient larger than 0 may be used as long as the weighting coefficient is a relatively low value. In addition, the weighting coefficient W0-$k$ for the band tomographic image TLj-k of a plurality of frequency bands that can be regarded as noise, such as not only the highest frequency band but also a frequency band next to the highest frequency band or even the next frequency band, may be reduced. In this manner, also in the second embodiment, it is possible to generate the composite two-dimensional image Gp with higher image quality and reduced noise.

Next, a fourth embodiment of the invention will be described. An image processing apparatus according to the fourth embodiment has the same configuration as the image processing apparatus according to the first embodiment, and only the processing to be performed is different. Accordingly, the detailed explanation of the apparatus will be omitted herein. In the first embodiment described above, the two-dimensional image generation unit 34 generates the band synthesized two-dimensional image GpL-1 of the highest frequency band by adding the corresponding pixel values of the band tomographic images TL1-1, TL2-1, . . . , TLm-1 generated on all the tomographic planes Tj. The fourth embodiment is different from the first embodiment in that the two-dimensional image generation unit 34 generates the band synthesized two-dimensional image GpL-k using a different projection method for each frequency band.

In the fourth embodiment, the two-dimensional image generation unit 34 generates the band synthesized two-dimensional image GpL-k using the minimum value projection method for the band tomographic image TLj-k from the highest frequency band to a predetermined frequency band, and generates the band synthesized two-dimensional image GpL-k using a projection method different from the minimum value projection method for the band tomographic image TLj-k of other frequency bands. As a projection method different from the minimum value projection method, it is possible to use the same method of addition or addition averaging as in the first embodiment.

In a case where the breast M is a subject, calcification is included in a projection image as a low-density minute region. Therefore, by generating the band synthesized two-dimensional image GpL-k using the minimum value projection method for the band tomographic image TLj-k from the highest frequency band to the predetermined frequency band, it is possible to generate a composite two-dimensional image in which a low-density minute region is emphasized. For this reason, particularly in a case where the subject is a breast, it is possible to accurately diagnose the calcification using the composite two-dimensional image Gp. In the fourth embodiment, the band synthesized two-dimensional image GpL-k may be generated using the minimum value projection method only for the highest frequency band.

In the second embodiment, the band synthesized two-dimensional image GpL-k may be generated using a different projection method for each frequency band. Specifically, the band synthesized two-dimensional image W0-$k$·GpL-k is generated using the minimum value projection method while weighting the band tomographic image TLj-k from the highest frequency band to the predetermined frequency band, and the band synthesized two-dimensional image W0-$k$·GpL-k is generated using a projection method different from the minimum value projection method for the band tomographic image TLj-k of other frequency bands. In this manner, it is possible to generate the composite two-dimensional image Gp in which a low-density minute region is emphasized. For this reason, particularly in a case where the subject is a breast, it is possible to accurately diagnose the calcification using the composite two-dimensional image Gp.

Also in the third and fourth embodiments described above, the band synthesized two-dimensional image GpL-k may be generated using a different projection method for each frequency band.

Figure 17:
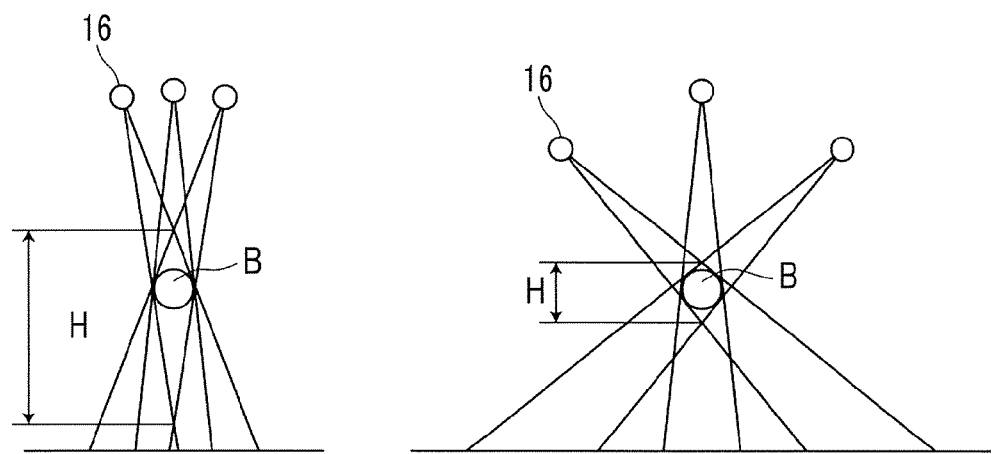
FIG. 17 is a diagram illustrating the relationship between an incidence angle and an artifact in the depth direction.

Next, a fifth embodiment of the invention will be described. An image processing apparatus according to the fifth embodiment has the same configuration as the image processing apparatus according to the first embodiment, and only the processing to be performed is different. Accordingly, the detailed explanation of the apparatus will be omitted herein. As shown in FIG. 17, in a case where the size of the structure B is the same, the range H where artifacts in the depth direction are generated increases as the incidence angle of X-rays with respect to the radiation detector 15 decreases. The fifth embodiment is different from the first embodiment in that the frequency synthesizing unit 35 changes the weighting coefficient Wk, by which the band synthesized two-dimensional image GpL-k is to be multiplied, according to the size of the movement range of the X-ray source 16. Also in the second embodiment, the two-dimensional image generation unit 34 may change the weighting coefficient W0-k, by which the band tomographic image TLj-k is to be multiplied, according to the size of the movement range of the X-ray source 16.

Specifically, the values of the weighting coefficients Wk and W0-k are set to decrease as the movement range of the X-ray source 16 decreases. Therefore, it is possible to further reduce the amount of artifacts in the depth direction of the structure when generating the composite two-dimensional image Gp. As a result, it is possible to generate the composite two-dimensional image Gp with higher image quality.

Also in the second to fourth embodiments, the weighting coefficient Wk by which the band synthesized two-dimensional image GpL-k is to be multiplied may be changed according to the size of the movement range of the X-ray source 16.

Next, a sixth embodiment of the invention will be described. An image processing apparatus according to the sixth embodiment has the same configuration as the image processing apparatus according to the first embodiment, and only the processing to be performed is different. Accordingly, the detailed explanation of the apparatus will be omitted herein. In the second embodiment described above, when generating the band synthesized two-dimensional image GpL-k, the two-dimensional image generation unit 34 weights the band tomographic image TLj-k of all the frequency bands with the same weighting coefficient W0-k to generate the band synthesized two-dimensional image GpL-k. The sixth embodiment is different from the second embodiment in that the band synthesized two-dimensional image is generated by reducing the weighting of a tomographic image of a tomographic plane at a position away from the radiation source at the time of imaging the subject.

Figure 18:
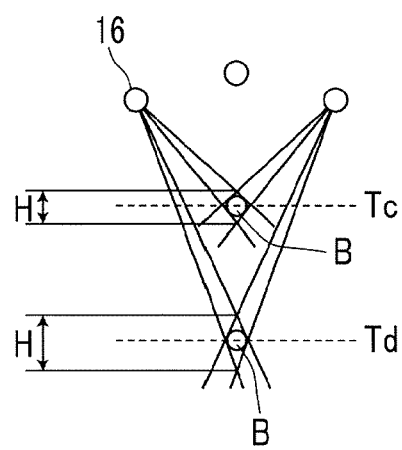
FIG. 18 is a diagram illustrating the change of a weighting coefficient in a fifth embodiment.

FIG. 18 is a diagram illustrating the change of the weighting coefficient in the sixth embodiment. As shown in FIG. 18, when a tomographic plane Tc at a position close to the X-ray source 16 in the subject M is compared with a tomographic plane Td at a position away from the X-ray source 16, the angle of incidence of X-rays on the structure B at the tomographic plane Td located at a position away from the X-ray source 16 is smaller than the angle of incidence of X-rays on the structure B at the tomographic plane Tc located at a position close to the X-ray source 16. For this reason, even if structures have the same size, a range in the depth direction in which artifacts are present increases as the distance of a structure from the X-ray source 16 increases. Therefore, by generating the band synthesized two-dimensional image Gp by reducing the weighting of a tomographic image of a tomographic plane at a position away from the X-ray source 16 at the time of imaging the subject, it is possible to further reduce artifacts in the depth direction of the structure. As a result, it is possible to generate the composite two-dimensional image Gp with higher image quality.

Even in a case where the third to fifth embodiments are applied to the second embodiment, a band synthesized two-dimensional image may be generated by reducing the weighting of a tomographic image of a tomographic plane at a position away from the radiation source at the time of imaging the subject.

Next, a seventh embodiment of the invention will be described. An image processing apparatus according to the seventh embodiment has the same configuration as the image processing apparatus according to the first embodiment, and only the processing to be performed is different. Accordingly, the detailed explanation of the apparatus will be omitted herein. The seventh embodiment is different from the first embodiment in that the frequency decomposition unit 33 frequency-decomposes the tomographic image TGj only in a direction in which the X-ray source 16 moves.

Figure 19:
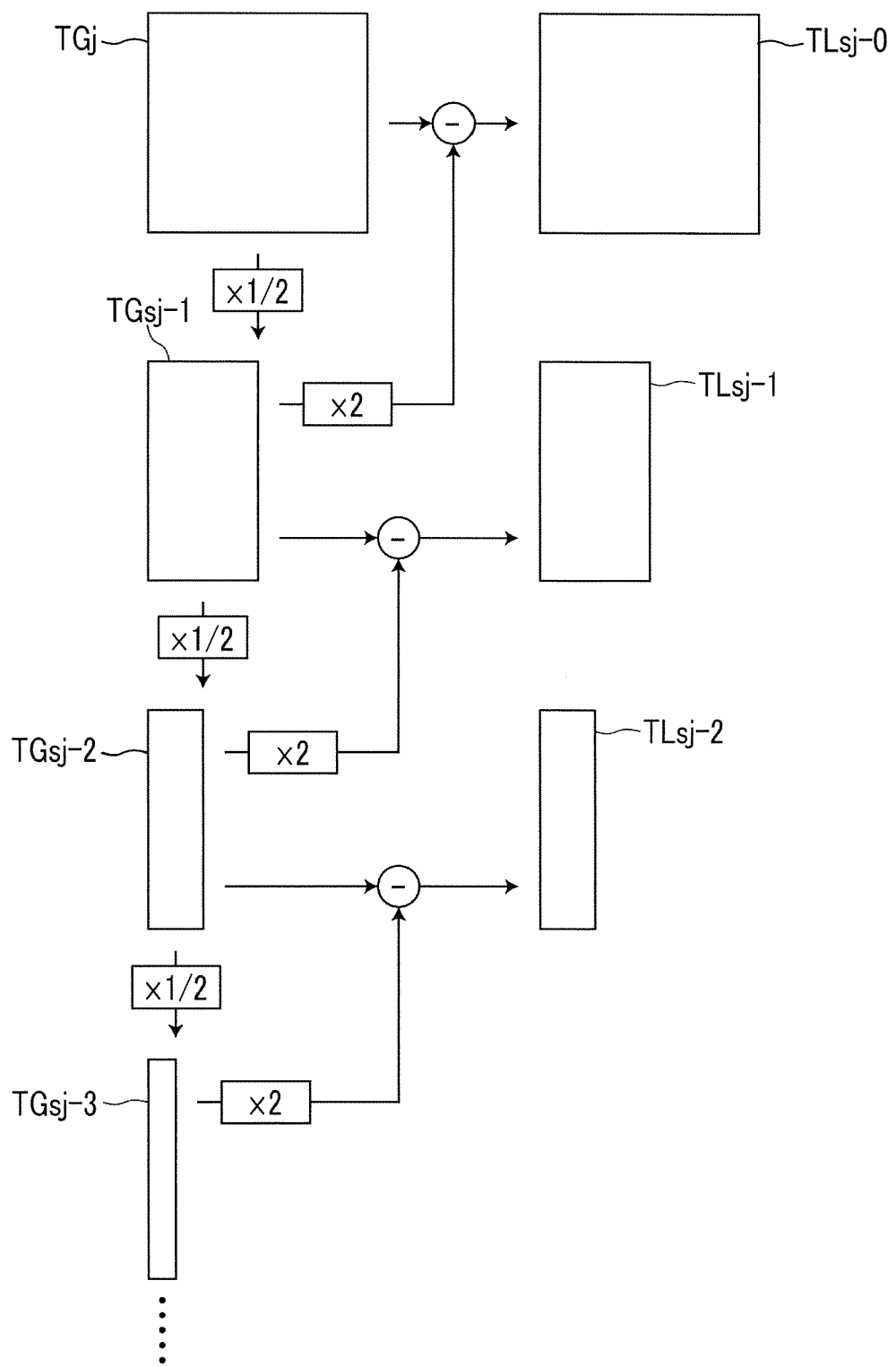
FIG. 19 is a diagram illustrating frequency decomposition in a seventh embodiment.

FIG. 19 is a diagram illustrating frequency decomposition in the seventh embodiment. In the seventh embodiment, first, the frequency decomposition unit 33 performs filtering processing on the tomographic image TGj of a certain frequency band with, for example, a Gaussian filter of $\sigma=1$ to minify the tomographic image TGj to ½ in the movement direction of the X-ray source 16, thereby generating a minified tomographic image TGsi-1 that is a Gaussian component. The movement direction of the X-ray source 16 is a horizontal direction in FIG. 19. The minified tomographic image TGsi-1 is obtained by minifying the tomographic image TGj to ½ in the movement direction of the X-ray source 16. Then, the frequency decomposition unit 33 performs an interpolation operation, such as cubic B-spline interpolation, to enlarge the minified tomographic image TGsi-1 twice so as to have the same size as the tomographic image TGj in the movement direction of the X-ray source 16, and subtracts the enlarged tomographic image TGsi-1 from the tomographic image TGj, thereby generating a band tomographic image TLsi-0 that is a Laplacian component of the highest frequency band.

Then, the frequency decomposition unit 33 performs filtering processing on the minified tomographic image TGsi-1 in the movement direction of the X-ray source 16 with a Gaussian filter of $\sigma=1$ to minify the minified tomographic image TGsi-1 to ½ in the movement direction of the X-ray source 16, thereby generating a minified tomographic image TGsi-2. Then, the frequency decomposition unit 33 enlarges the minified tomographic image TGsi-2 twice in the movement direction of the X-ray source 16 so as to have the same size as the minified tomographic image TGsi-1, and subtracts the enlarged minified tomographic image TGsi-2 from the minified tomographic image TGsi-1, thereby generating a band tomographic image TLsi-1 of the first frequency band. By repeating the above-described processing until a band tomographic image of a desired frequency band is generated, a band tomographic image TLsi-k (k=0 to a: a is the number of bands) of a plurality of frequency bands is generated. A plurality of band tomographic images TLsi-k having different frequency bands may be generated by using other methods of multi-resolution conversion, such as wavelet transformation.

Since the seventh embodiment is the same as the first embodiment except that the processing performed by the reconstruction unit 32, the two-dimensional image generation unit 34, and the frequency synthesizing unit 35 is for the band tomographic image TLsi-k generated by frequency decomposition in the movement direction of the X-ray source 16, the detailed explanation thereof will be omitted herein.

As described above, in the seventh embodiment, since each of the plurality of tomographic images TGj is subjected to frequency decomposition only in the movement direction of the X-ray source 16, it is possible to reduce the amount of calculation for frequency decomposition, generation of a composite two-dimensional image, and frequency synthesis.

Also in the second embodiment described above, the frequency decomposition unit 33 may frequency-decompose the tomographic image TGj only in the movement direction of the X-ray source 16 as in the seventh embodiment. In addition, also in the third to sixth embodiments described above, the frequency decomposition unit 33 may frequency-decompose the tomographic image TGj only in the movement direction of the X-ray source 16 as in the seventh embodiment.

Figure 20:
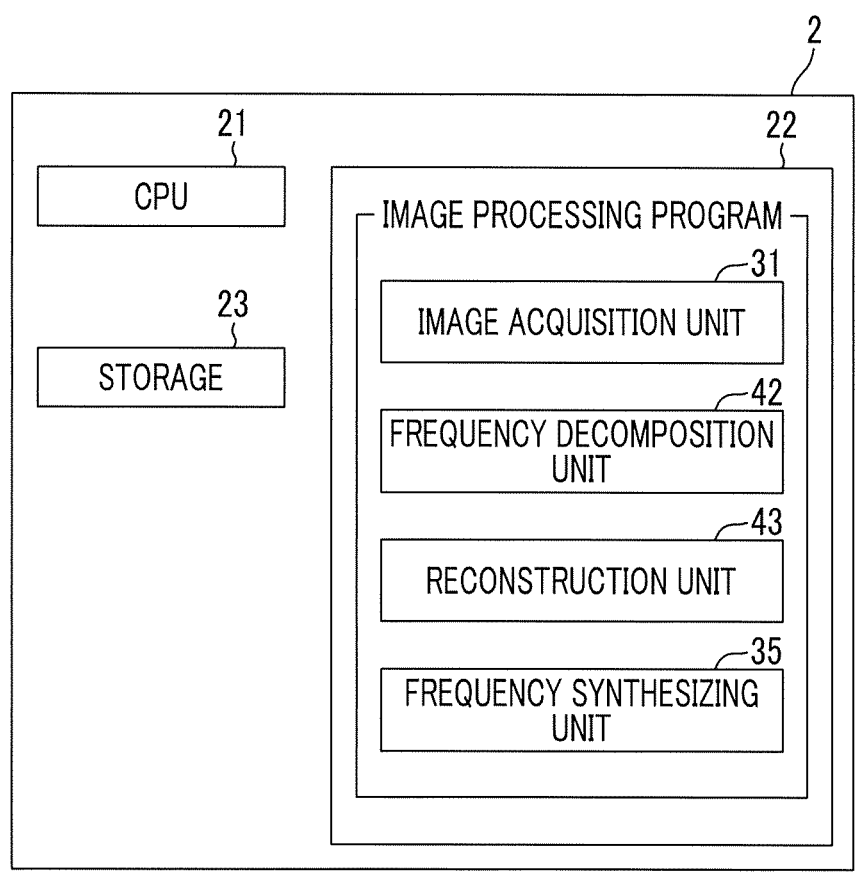
FIG. 20 is a diagram showing the schematic configuration of an image processing apparatus according to an eighth embodiment of the invention.

Next, an eighth embodiment of the invention will be described. FIG. 20 is a diagram showing the schematic configuration of an image processing apparatus according to the eighth embodiment of the invention. In FIG. 20, the same components as in FIG. 3 are denoted by the same reference numbers, and the detailed explanation thereof will be omitted. In the image processing apparatus according to the eighth embodiment of the invention, processing for generating the band tomographic image TLj-k is different from that in the first and second embodiments. Therefore, the image processing apparatus according to the eighth embodiment includes a frequency decomposition unit 42 and a reconstruction unit 43 instead of the reconstruction unit 32 and the frequency decomposition unit 33. The frequency decomposition unit 42 and the reconstruction unit 43 form a band tomographic image generation unit of the invention.

Figure 21:
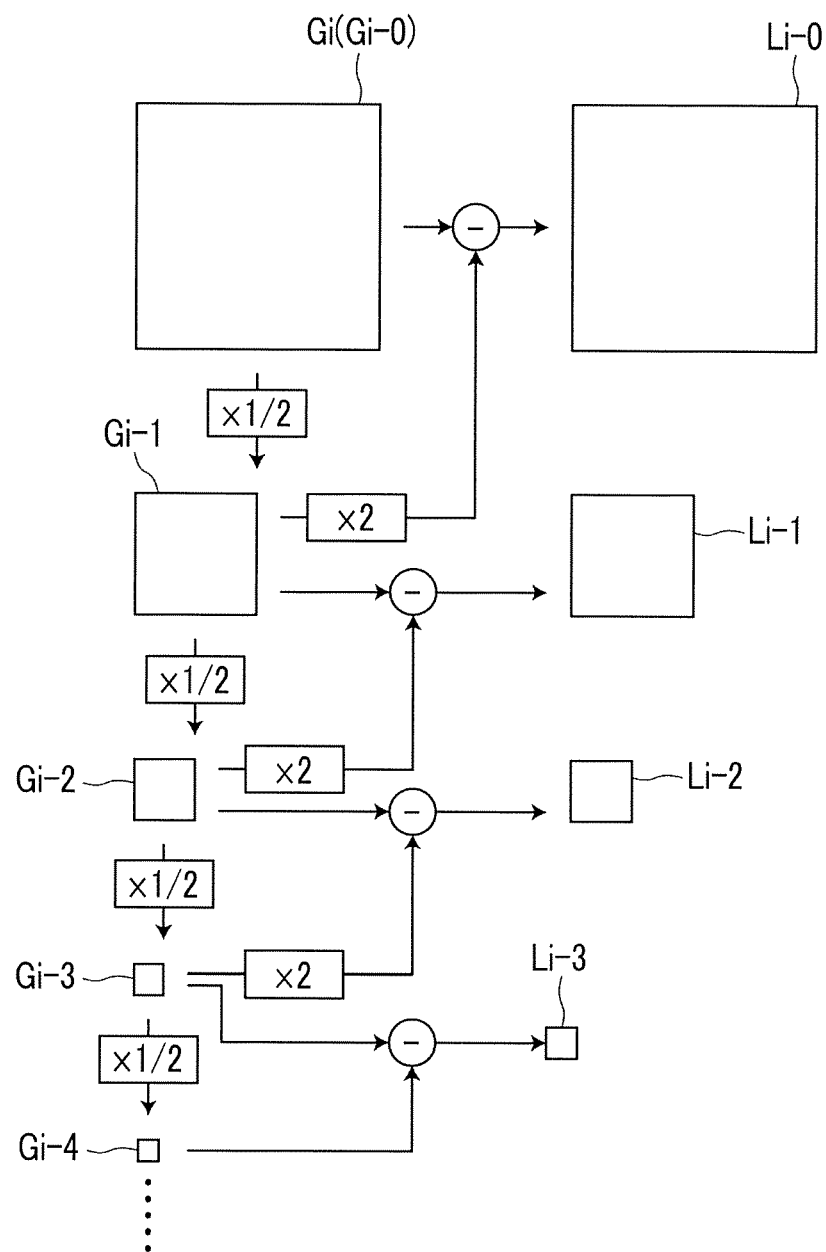
FIG. 21 is a diagram illustrating frequency decomposition performed by a frequency decomposition unit in the eighth embodiment.

In the eighth embodiment, the frequency decomposition unit 42 frequency-decomposes each of the plurality of projection images Gi to acquire a plurality of band projection images, which show frequency components of each of the plurality of frequency bands, for each of the plurality of projection images Gi. FIG. 21 is a diagram illustrating frequency decomposition performed by the frequency decomposition unit 42 in the eighth embodiment. First, the frequency decomposition unit 42 performs filtering processing on the projection image Gi of a certain frequency band with, for example, a Gaussian filter of σ=1 to minify the projection image Gi to ½, thereby generating a minified image Gi-1 that is a Gaussian component. The minified image Gi-1 is obtained by minifying the projection image Gi to ½. In the following description, the projection image Gi may be referred to as a projection image Gi-0 for convenience. Then, the frequency decomposition unit 42 performs an interpolation operation, such as cubic B-spline interpolation, to enlarge the minified image Gi-1 twice so as to have the same size as the projection image Gi-0, and subtracts the enlarged minified image Gi-1 from the projection image Gi-0, thereby generating a band projection image Li-0 that is a Laplacian component of the highest frequency band.

Then, the frequency decomposition unit 42 performs filtering processing on the minified image Gi-1 with a Gaussian filter of σ=1 to minify the minified image Gi-1 to ½, thereby generating a minified image Gi-2. Then, the frequency decomposition unit 33 enlarges the minified image Gi-2 twice so as to have the same size as the minified image Gi-1, and subtracts the enlarged minified image Gi-2 from the minified image Gi-1, thereby generating a band projection image Li-1 of the first frequency band. By repeating the above-described processing until a band projection image of a desired frequency band is generated, a band projection image Li-k (k=0 to a: a is the number of bands) of a plurality of frequency bands is generated.

The reconstruction unit 43 reconstructs the band projection image Li-k of a plurality of frequency bands for each frequency band to acquire a plurality of band tomographic images, which show frequency components of each of the plurality of frequency bands, for each of a plurality of tomographic planes of the breast M. Specifically, the reconstruction unit 43 generates the band tomographic image TLj-k on each of a plurality of tomographic planes Tj (j=1 to m: m is the number of tomographic planes) by reconstructing the band projection image Li-k for each frequency band using a known back projection method, such as a simple back projection method or a filtered back projection method, a shift addition method, a known CT reconstruction method, or the like as in the first embodiment described above. The band tomographic image TLj-k generated in the eighth embodiment is the same as the band tomographic image generated by the frequency decomposition unit 33 in the first and second embodiments described above.

In the eighth embodiment, after generating the band tomographic image TLj-k in this manner, a band synthesized two-dimensional image and a composite two-dimensional image are generated in the same manner as in the first and second embodiments described above.

Also in the third to seventh embodiments, the band tomographic image TLj-k may be generated in the same manner as in the eighth embodiment.

Also in the eighth embodiment, when generating a band projection image, filtering may be performed only in the movement direction of the X-ray source 16 as in the seventh embodiment. Therefore, it is possible to reduce the amount of calculation for frequency decomposition, generation of a composite two-dimensional image, and frequency synthesis.

In each of the embodiments described above, tomosynthesis imaging is performed using the breast M as a subject. However, it is needless to say that the invention can also be applied to a case of performing tomosynthesis imaging on a subject other than the breast.

In each of the embodiments described above, only the X-ray source 16 is moved. However, depending on the imaging apparatus, it is possible to move the X-ray source 16 and the radiation detector 15 in synchronization with each other. In such a case, therefore, the X-ray source 16 and the radiation detector 15 may be moved in synchronization with each other. Alternatively, the X-ray source 16 may be fixed and only the radiation detector 15 may be moved.

In each of the embodiments described above, the invention is applied to the imaging apparatus that performs tomosynthesis imaging. However, the invention can be applied to an arbitrary imaging apparatus that acquires a plurality of projection images by imaging a subject at a plurality of radiation source positions. For example, the invention can also be applied to a CT imaging apparatus in which a radiation source and a radiation detector are disposed so as to face each other around a subject and radiation is emitted from various angles by rotating the radiation source and the radiation detector around the subject, thereby acquiring a plurality of projection images.

In each of the embodiments described above, the trajectory of the X-ray source 16 is an arc. However, the trajectory of the X-ray source 16 may be a straight line.

Hereinafter, the effect of the embodiment of the invention will be described.

In a relatively high frequency band including the highest frequency band, noise is often included in the band synthesized two-dimensional image and the band tomographic image. Therefore, by generating the composite two-dimensional image by reducing the weighting of the band synthesized two-dimensional image from the highest frequency band to a predetermined frequency band, it is possible to generate the composite two-dimensional image with higher image quality and reduced noise. In addition, by generating the band synthesized two-dimensional image by reducing the weighting of the band tomographic image from the highest frequency band to a predetermined frequency band, it is possible to generate the composite two-dimensional image with higher image quality and reduced noise.

By generating the band synthesized two-dimensional image using a different projection method for each frequency band, it is possible to generate a composite two-dimensional image taking advantage of the features of various projection methods.

In particular, a composite two-dimensional image in which a low-density minute region is emphasized can be generated by generating a band synthesized two-dimensional image using the minimum value projection method for a band tomographic image from the highest frequency band to a predetermined frequency band and generating a band synthesized two-dimensional image using a projection method different from the minimum value projection method for band tomographic images of other frequency bands. For this reason, particularly in a case where the subject is a breast, it is possible to accurately diagnose the calcification using the composite two-dimensional image.

At the time of imaging, at a position of the subject close to the radiation source and a position of the subject away from the radiation source, radiation is emitted at a relatively small incidence angle as the distance of a portion from the radiation source increases. As a result, as the distance of a structure from the radiation source at the time of imaging the subject increases, the range in the depth direction of the structure in which artifacts are present increases. Therefore, by generating the band synthesized two-dimensional image by reducing the weighting of a tomographic image of a tomographic plane at a position away from the radiation source at the time of imaging the subject, it is possible to further reduce artifacts in the depth direction of the structure. As a result, it is possible to generate the composite two-dimensional image with higher image quality.

If the relative movement range of the radiation source with respect to the detection unit is small, the range in the depth direction of the structure in which artifacts are present is large. Therefore, by generating the band synthesized two-dimensional image by reducing the weighting as the relative movement range of the radiation source with respect to the detection unit decreases, it is possible to further reduce artifacts in the depth direction of the structure. As a result, it is possible to generate the composite two-dimensional image with higher image quality.

By frequency-decomposing each of a plurality of tomographic images in a specific direction in the tomographic image, it is possible to reduce the amount of calculation for frequency decomposition and frequency synthesis.

What is claimed is:

1. An image processing apparatus, comprising:
   image acquisition unit for acquiring a plurality of projection images corresponding to a plurality of radiation source positions, the plurality of projection images being captured by moving a radiation source relative to detection unit and emitting radiation to a subject at the plurality of radiation source positions due to movement of the radiation source;
   band tomographic image generation unit for generating a plurality of band tomographic images, which show frequency components of each of a plurality of frequency bands, for each of a plurality of tomographic planes of the subject based on the plurality of projection images;
   two-dimensional image generation unit for generating a band synthesized two-dimensional image by projecting the plurality of band tomographic images for each of the frequency bands; and
   frequency synthesizing unit for generating a composite two-dimensional image by weighting the band synthesized two-dimensional image and performing frequency synthesis for each of the frequency bands.

2. The image processing apparatus according to claim 1, wherein the frequency synthesizing unit generates the composite two-dimensional image by reducing a weighting of a band synthesized two-dimensional image of a low frequency band.

3. The image processing apparatus according to claim 1, wherein the frequency synthesizing unit generates the composite two-dimensional image by reducing a weighting of a band synthesized two-dimensional image from a highest frequency band to a predetermined frequency band.

4. The image processing apparatus according to claim 1, wherein the two-dimensional image generation unit generates the band synthesized two-dimensional image using a different projection method for each of the frequency bands.

5. The image processing apparatus according to claim 4, wherein the two-dimensional image generation unit generates the band synthesized two-dimensional image using a minimum value projection method for a band tomographic image from a highest frequency band to a predetermined frequency band, and generates the band synthesized two-dimensional image using a projection method different from the minimum value projection method for band tomographic images of other frequency bands.

6. The image processing apparatus according to claim 1, wherein the two-dimensional image generation unit generates the band synthesized two-dimensional image by reducing a weighting as a relative movement range of the radiation source with respect to the detection unit decreases.

7. The image processing apparatus according to claim 1, wherein the band tomographic image generation unit comprises:
   reconstruction unit for generating a plurality of tomographic images on each of the plurality of tomographic planes by reconstructing the plurality of projection images; and
   frequency decomposition unit for generating the plurality of band tomographic images by frequency-decomposing each of the plurality of tomographic images.

8. The image processing apparatus according to claim 7, wherein the frequency decomposition unit frequency-decomposes each of the plurality of tomographic images in a specific direction in the tomographic image.

9. The image processing apparatus according to claim 8, wherein the specific direction is a direction in which the radiation source is moved relative to the detection unit.

10. The image processing apparatus according to claim 1, wherein the band tomographic image generation unit comprises:
frequency decomposition unit for generating a plurality of band projection images, which show frequency components of each of the plurality of frequency bands, for each of the plurality of projection images by frequency-decomposing each of the plurality of projection images; and
reconstruction unit for generating the plurality of band tomographic images by reconstructing the plurality of band projection images for each of the frequency bands.

11. The image processing apparatus according to claim 10, wherein the frequency decomposition unit frequency-decomposes each of the plurality of tomographic images in a specific direction in the projection image.

12. An image processing apparatus, comprising:
image acquisition unit for acquiring a plurality of projection images corresponding to a plurality of radiation source positions, the plurality of projection images being captured by moving a radiation source relative to detection unit and emitting radiation to a subject at the plurality of radiation source positions due to movement of the radiation source;
band tomographic image generation unit for generating a plurality of band tomographic images, which show frequency components of each of a plurality of frequency bands, for each of a plurality of tomographic planes of the subject based on the plurality of projection images;
two-dimensional image generation unit for generating a band synthesized two-dimensional image by weighting the plurality of band tomographic images and performing projection for each of the frequency bands; and
frequency synthesizing unit for generating a composite two-dimensional image by performing frequency synthesis of the band synthesized two-dimensional image.

13. The image processing apparatus according to claim 12, wherein the two-dimensional image generation unit generates the band synthesized two-dimensional image by reducing a weighting of a band tomographic image of a low frequency band.

14. The image processing apparatus according to claim 12, wherein the two-dimensional image generation unit generates the band synthesized two-dimensional image by reducing a weighting of a band tomographic image from a highest frequency band to a predetermined frequency band.

15. The image processing apparatus according to claim 12, wherein the two-dimensional image generation unit generates the band synthesized two-dimensional image using a different projection method for each of the frequency bands.

16. The image processing apparatus according to claim 15, wherein the two-dimensional image generation unit generates the band synthesized two-dimensional image using a minimum value projection method for a band tomographic image from a highest frequency band to a predetermined frequency band, and generates the band synthesized two-dimensional image using a projection method different from the minimum value projection method for band tomographic images of other frequency bands.

17. The image processing apparatus according to claim 12, wherein the two-dimensional image generation unit generates the band synthesized two-dimensional image by reducing a weighting of a tomographic image at a position away from the radiation source at the time of imaging the subject.

18. An image processing method, comprising:
acquiring a plurality of projection images corresponding to a plurality of radiation source positions, the plurality of projection images being captured by moving a radiation source relative to detection unit and emitting radiation to a subject at the plurality of radiation source positions due to movement of the radiation source;
generating a plurality of band tomographic images, which show frequency components of each of a plurality of frequency bands, for each of a plurality of tomographic planes of the subject based on the plurality of projection images;
generating a band synthesized two-dimensional image by projecting the plurality of band tomographic images for each of the frequency bands; and
generating a composite two-dimensional image by weighting the band synthesized two-dimensional image and performing frequency synthesis for each of the frequency bands.

19. An image processing method, comprising:
acquiring a plurality of projection images corresponding to a plurality of radiation source positions, the plurality of projection images being captured by moving a radiation source relative to detection unit and emitting radiation to a subject at the plurality of radiation source positions due to movement of the radiation source;
generating a plurality of band tomographic images, which show frequency components of each of a plurality of frequency bands, for each of a plurality of tomographic planes of the subject based on the plurality of projection images;
generating a band synthesized two-dimensional image by weighting the plurality of band tomographic images and performing projection for each of the frequency bands; and
generating a composite two-dimensional image by performing frequency synthesis of the band synthesized two-dimensional image.

20. A non-transitory computer-readable recording medium having stored therein an image processing program causing a computer to execute:
a step of acquiring a plurality of projection images corresponding to a plurality of radiation source positions, the plurality of projection images being captured by moving a radiation source relative to detection unit and emitting radiation to a subject at the plurality of radiation source positions due to movement of the radiation source;

a step of generating a plurality of band tomographic images, which show frequency components of each of a plurality of frequency bands, for each of a plurality of tomographic planes of the subject based on the plurality of projection images;

a step of generating a band synthesized two-dimensional image by projecting the plurality of band tomographic images for each of the frequency bands; and a step of generating a composite two-dimensional image by weighting the band synthesized two-dimensional image and performing frequency synthesis for each of the frequency bands.

21. A non-transitory computer-readable recording medium having stored therein an image processing program causing a computer to execute:

a step of acquiring a plurality of projection images corresponding to a plurality of radiation source positions, the plurality of projection images being captured by moving a radiation source relative to detection unit and emitting radiation to a subject at the plurality of radiation source positions due to movement of the radiation source;

a step of generating a plurality of band tomographic images, which show frequency components of each of a plurality of frequency bands, for each of a plurality of tomographic planes of the subject based on the plurality of projection images;

a step of generating a band synthesized two-dimensional image by weighting the plurality of band tomographic images and performing projection for each of the frequency bands; and a step of generating a composite two-dimensional image by performing frequency synthesis of the band synthesized two-dimensional image.

\* \* \* \* \*